US012766100B2

(12) United States Patent
Bansal et al.

(10) Patent No.: US 12,766,100 B2
(45) Date of Patent: Oct. 20, 2026

(54) IN VIVO TARGETING OF EXTRACELLULAR VESICLES

(71) Applicant: Mayo Foundation for Medical Education and Research, Rochester, MN (US)

(72) Inventors: Aditya Bansal, Rochester, MN (US); Timothy R. DeGrado, Rochester, MN (US); Mukesh K. Pandey, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 180 days.

(21) Appl. No.: 17/992,209

(22) Filed: Nov. 22, 2022

(65) Prior Publication Data

US 2023/0107354 A1 Apr. 6, 2023

Related U.S. Application Data

(62) Division of application No. 16/834,048, filed on Mar. 30, 2020, now Pat. No. 11,510,876.

(60) Provisional application No. 62/826,039, filed on Mar. 29, 2019.

(51) Int. Cl.

| | |
|---|---|
| ***A61K 9/1271*** | (2025.01) |
| ***A61K 9/1277*** | (2025.01) |
| ***A61K 47/55*** | (2017.01) |
| ***A61K 47/66*** | (2017.01) |

(52) U.S. Cl.

CPC .......... *A61K 9/1271* (2013.01); *A61K 9/1277* (2013.01); *A61K 47/55* (2017.08); *A61K 47/66* (2017.08)

(58) Field of Classification Search

None

See application file for complete search history.

(56) References Cited

U.S. PATENT DOCUMENTS

| | | | |
|---|---|---|---|
| 8,188,074 | B2 | 5/2012 | Brown |
| 8,273,577 | B2 | 9/2012 | Yonehara |
| 9,005,888 | B2 | 4/2015 | Antes |
| 9,835,626 | B2 | 12/2017 | Schroit |

(Continued)

FOREIGN PATENT DOCUMENTS

| | | | | |
|---|---|---|---|---|
| WO | 2013/048734 A1 | | 4/2013 | |
| WO | 2016/191556 A1 | | 12/2016 | |
| WO | WO-2019213706 A1 | * | 11/2019 | ............. A61K 35/12 |

OTHER PUBLICATIONS

Amedeo Vetere, Amit Choudhary, Sean M. Burns and Bridget K. Wagner. "Targeting the pancreatic B-cell to treat diabetes." Nature Reviews Drug Discovery, vol. 13, Apr. 2014, pp. 278-289. (Year: 2014).*

(Continued)

*Primary Examiner* — Isaac Shomer

(74) *Attorney, Agent, or Firm* — Quarles & Brady LLP

(57) ABSTRACT

A method for chemically induced homing of extracellular vesicles (EVs) to a specific tissue or organ in a subject for either treatment or diagnosis of a medical condition, the method comprising administering to the subject an amount of a homing agent. The homing agent is at least one of a derivative of poly(ethylene glycol), or a derivative of phenothiazine. The EVs are homed to the homing agent in the subject.

29 Claims, 13 Drawing Sheets

(56) References Cited

U.S. PATENT DOCUMENTS

| | | | | |
|---|---|---|---|---|
| 2008/0193372 | A1* | 8/2008 | Lanza | A61K 51/1234 424/9.4 |
| 2008/0193376 | A1 | 8/2008 | Tawakol | |
| 2010/0092524 | A1* | 4/2010 | Taylor | A61K 39/4644 424/277.1 |
| 2010/0216691 | A1* | 8/2010 | Madsen | A61P 3/00 530/303 |
| 2014/0256626 | A1* | 9/2014 | Santi | A61K 47/60 530/324 |
| 2016/0331686 | A1 | 11/2016 | Polach | |
| 2017/0051282 | A1 | 2/2017 | Gingeras | |
| 2017/0087195 | A1* | 3/2017 | Kim | A61P 3/06 |

OTHER PUBLICATIONS

Vijay Bhaskar Reddy Konala et al. "The current landscape of the mesenchymal stromal cell secretome: A new paradigm for cell-free regeneration." Cytotherapy, vol. 18, 2016, pp. 13-24. (Year: 2016).*
Daniela Hutanu, Mark D Frishberg, Lihong Guo and Costel C Darie. "Recent Applications of Polyethylene Glycols (PEGs) and PEG Derivatives." Modern Chemistry & Applications, vol. 2-3, 2014, ISSN 2329-6798, pp. 1-6. (Year: 2014).*
Bansal A, et al. Novel (89)Zr cell labeling approach for PET-based cell trafficking studies. EJNMMI Res. 2015; 5: 19.
Choi, H,, et al. "Noninvasive imaging of radiolabeled exosome-mimetic nanovesicle using 99m Tc-HMPAO." Scientific reports 5.1 (2015): 1-10.
Gupta, S., et al. "Biocatalytic approach for the synthesis of glycerol-based macroamphiphiles and their self-assembly to micellar nanotransporters." Macromolecular Chemistry and Physics 211.2 (2010): 239-244.
Holland JP, et al. Standardized methods for the production of high specific-activity zirconium-89. Nucl Med Biol. 2009; 36: 729-39.
Iessi, E, et al. "Acridine Orange/exosomes increase the delivery and the effectiveness of Acridine Orange in human melanoma cells: A new prototype for theranostics of tumors." Journal of enzyme inhibition and medicinal chemistry 32.1 (2017): 648-657.
Kusuzaki, K,, et al. "Natural extracellular nanovesicles and photodynamic molecules: is there a future for drug delivery?." Journal of enzyme inhibition and medicinal chemistry 32.1 (2017): 908-916.
Ohno S. et al. Systemically injected exosomes targeted to EGFR deliver antitumor microRNA to breast cancer cells. Mol Ther. Jan. 2013;21(1):185-91.
Pandey MK, et al. "Design and biocatalytic synthesis of pluronics-based nanomicellar self-assembly systems for drug encapsulation applications." Journal of Macromolecular Science, Part A: Pure and Applied Chemistry 47.8 (2010): 788-793.
Pandey MK, et al. "Design and Synthesis of Novel Pegylated 4-Methylcoumarins." Journal of Macromolecular Science, Part A 44.12 (2007): 1293-1298.
Pandey MK, et al. "Design and synthesis of perfluorinated amphiphilic copolymers: Smart nanomicelles for theranostic applications." Polymer 52.21 (2011): 4727-4735.
Pandey MK, et al. "Design, synthesis and anti-inflammatory evaluation of PEGylated 4-methyl and 4, 8-dimethylcoumarins." European journal of pharmaceutical sciences 39.1-3 (2010): 134-140.
Pandey MK, et al. "Design, synthesis and evaluation of novel PEGylated curcumin analogs as potent Nrf2 activators In human bronchial epithelial cells." European Journal of Pharmaceutical Sciences 43.1-2 (2011): 16-24.
Pandey MK, et al. Improved production and processing of 8?Zr using a solution target. Nucl Med Biol. Jan. 2016;43(1):97-100.
Pandey MK, et al. Production of 89Zr via the 89Y(p,n)89Zr reaction in aqueous solution: effect of solution composition on in-target chemistry. Nucl Med Biol. 2014; 41: 309-16.
Vandergriff A. et al. Targeting regenerative exosomes to myocardial infarction using cardiac homing peptide. Theranostics. Feb. 14, 2018;8(7):1869-1878.
K. Orth, D. Russ, G. Beck, A. Ruck, and H. G. Beger. "Photochemotherapy of experimental colonic tumours with intra-tumorally applied methylene blue." Langenbeck's Arch Surg, vol. 383 (1998), pp. 276-281.
Timothy M. Baran, Benjamin R. Giesselman, Rui Hu, Merrill A. Biel, and Thomas H. Foster. "Factors Influencing Tumor Response to Photodynamic Therapy Sensitized by Intratumor Administration of Methylene Blue." Lasers in Surgery and Medicine, vol. 42, 2010, pp. 728-735.
Kirste J. Mellish, Russell D. Cox, David I. Vernon, John Griffiths and Stanley B. Brown. "In Vitro Photodynamic Activity of a Series of Methylene Blue Analogues." Photochemistry and Photobiology, vol. 75(4), 2002, pp. 392-397.
US Food and Drug Administration. Prescribing Information for Provayblue. https://www.accessdata.fda.gov/drugsatfda_docs/label/2016/204630s000lbl.pdf accessed Nov. 30, 2021, pp. 1-10.

* cited by examiner

IN VIVO TARGETING OF EXTRACELLULAR VESICLES

CROSS-REFERENCE TO RELATED APPLICATIONS

The present application is a divisional application of U.S. patent application Ser. No. 16/834,048 filed Mar. 30, 2020, which is based on and claims priority to U.S. Provisional Patent Application No. 62/826,039, filed Mar. 29, 2019, which are hereby incorporated by reference herein in their entirety for all purposes.

STATEMENT OF FEDERALLY SPONSORED RESEARCH OR DEVELOPMENT

Not applicable.

BACKGROUND

Extracellular vesicles ("EVs") are heterogenous cell derived vesicles with a size spanning anywhere from 30 to 2000 nanometers. They have pleiotropic biological functions and are heterogenous in composition. Although the term extracellular vesicles broadly encompasses all membrane bound vesicles, other more specific membrane vesicle terms are determined by their origin, size, function, markers, and/or contents stored within its internal volume. Examples of these terms include but are not limited to: exosomes, ectosomes, microvesicles, microparticles, macrovesicles, dexosomes, exosome like vesicles, exovesicles, nanovesicles, membrane particles, oncosomes, prominosomes, prostasomes, shedding microvesicles/vesicles, epididymosomes, archeosomes, tolerosomes, apoptotic bodies, budding vesicles, argosomes, blebbing vesicles, budding vesicles, extracellular membrane vesicles, membrane vesicles, etc. As indicated above, EVs are heterogeneous in composition with a variety of biologically derived contents stored within its internal volume. For example, these biologically derived contents can include lipids, amino acids, proteins, peptides, nucleic acids, carbohydrates, enzymes, RNA, mRNA, miRNA, DNA, metabolites, inorganic salts, cytoplasm, signaling molecules, etc. Due to the membrane derived nature of EVs, EVs can also contain transmembrane proteins, or integral membrane proteins that can span a portion or the entire thickness of the membrane, and can contain cell to cell communication receptors. Additionally, EVs are created and/or present in all tissues of the human body such as organs, biological fluids, sweat, lymph, blood, urine, the interstitial space, etc. Thus, EVs generally are involved in cell to cell communication pathways and other higher-ordered communication pathways such as cross talk between organs/tissues including overall cell, tissue, and biological system homeostasis.

As described above, EVs have unique properties due to their cargo, origin, surface charge and size (individually or in combination), allowing them to have a role, which impacts both diagnostics and therapies (e.g., biological processes and interventions such as tissue regeneration therapy, tissue remodeling, immunotherapies, immune response, disease processes, drug delivery, tumor growth and metastasis, etc.). The unique properties of EVs can be at least partially attributed to their biological structure, which includes (or can include) a lipid bilayer, transmembrane proteins, lipids, proteins, peptides, amino acids, nucleic acids, enzymes, RNA, mRNA, miRNA, DNA, metabolites, inorganic salts, cytoplasm, signaling molecules and other cellular components that mediate cell-to-cell communication. Unique to EVs and to other hydrophobic molecules, EVs can access all tissues, including the brain via blood-brain-barrier transport. Additionally and importantly, EVs have a low toxicity profile that supports other therapeutic applications where the EVs function as carriers of various therapeutic molecules. Similarly, other therapies involving the modification of EVs using targeting peptides (e.g., engineered EVs) to target specific locations within a subject currently exist, although the therapeutic potential/effectiveness of these modified EVs are unknown.

Great advances have been made over the last 20 years in understanding the importance of EVs but the approach to understanding EV biogenesis and EV-based therapies and diagnostics have primarily been passive and observational. For example, in therapy, EVs are administered locally or systemically, hoping some will reach the disease target for inducing therapy. For diagnostics, one relies on natural abundance of the EVs in tissues, urine, biological fluids for identifying disease specific markers.

SUMMARY

Some embodiments of the disclosure provide a method for chemically induced homing of extracellular vesicles (EVs) to a specific tissue or organ in a subject for either treatment or diagnosis of a medical condition, the method comprising: (a) administering to the subject an amount of a homing agent, wherein the homing agent is at least one of a derivative of poly(ethylene glycol), or a derivative of phenothiazine; and (b) administering EVs to the subject, wherein the EVs are homed to the homing agent in the subject and wherein (a) and (b) can be interchanged.

In some embodiments, the homing agent is poly(ethylene glycol), or a derivative thereof.

In some embodiments, the homing agent is poly(ethylene glycol) or the derivative of poly(ethylene glycol), wherein a molecular weight of the derivative of the poly(ethylene glycol) is 150 to 2000 Daltons, wherein the derivative of poly(ethylene glycol) has end groups being hydroxyl groups, and wherein at least one end group is not a hydroxyl group. In some embodiments, the derivative of poly(ethylene glycol) has varying chain lengths. In some embodiments, the poly(ethylene glycol) has various branching.

In some embodiments, the homing agent is a polymer being a polypropylene oxide ("PPO"), a polypropylene glycol ("PPG"), PEG/PPO containing copolymers (e.g., block copolymers of PEG or block copolymers of PPO PPG, etc.).

In some embodiments, the homing agent is a derivative of phenothiazine, and wherein the derivative of phenothiazine is methylene blue.

In some embodiments, the derivative of phenothiazine is selected from a group consisting of Formula (II), a tautomer of Formula (II), a stereoisomer of Formula (II), a salt of Formula (II), and combinations thereof, wherein Formula (II) is:

(II)

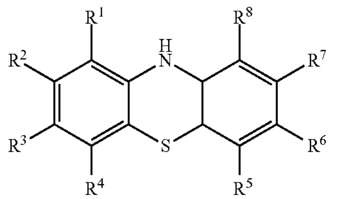

wherein each of $R^1$, $R^2$, $R^3$, $R^4$, $R^5$, $R^6$, $R^7$, and $R^8$ is independently an atom or a group of atoms.

In some embodiments, $R^1$, $R^2$, $R^3$, $R^4$, $R^5$, $R^6$, $R^7$, and $R^8$ is independently selected from a group consisting of hydrogen, substituted or unsubstituted alkyl, substituted or unsubstituted alkyl carbonyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, OH, halogen, substituted or unsubstituted alkoxy, substituted or unsubstituted amino, and substituted or unsubstituted carboxylate.

In some embodiments, the derivative of phenothiazine is selected from a group consisting of Formula (III), a tautomer of Formula (III), a stereoisomer of Formula (III), a salt of Formula (III), and combinations thereof, wherein Formula (III) is:

(III)

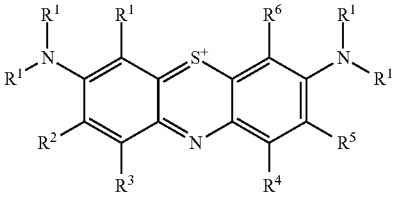

wherein each of $R^1$, $R^2$, $R^3$, $R^4$, $R^5$, $R^6$, $R^7$, and $R^8$ is independently an atom or a group of atoms.

In some embodiments, $R^1$, $R^2$, $R^3$, $R^4$, $R^5$, $R^6$, $R^7$, and $R^8$ is independently selected from a group consisting of hydrogen, substituted or unsubstituted alkyl, substituted or unsubstituted alkyl carbonyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, OH, halogen, substituted or unsubstituted alkoxy, substituted or unsubstituted amino, and substituted or unsubstituted carboxylate.

In some embodiments, at least one atom in the derivative of poly(ethylene glycol) or the derivative of phenothiazine is replaced with a positron emitter selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{211}At$, $^{75}Br$, $^{76}Br$, $^{82}Rb$, $^{43}Sc$, $^{44}Sc$, $^{86}Y$, $^{89}Zr$, $^{90}Nb$, $^{94m}Tc$, $^{110m}In$, $^{118}Sb$, and $^{124}I$.

In some embodiments, at least one atom in the derivative of poly(ethylene glycol) or the derivative of phenothiazine is replaced with a photon emitter selected from the group consisting of $^{67}Ga$, $^{99m}Tc$, $^{111}In$, $^{123}I$, $^{125}I$, $^{131}I$, and $^{201}Tl$.

In some embodiments, at least one atom in the derivative of poly(ethylene glycol) or the derivative of phenothiazine is replaced with a magnetic resonance imaging contrast agent selected from the group consisting of ions of gadolinium, manganese, and iron.

In some embodiments, the EVs include an associated imaging agent, and the method further comprising acquiring imaging data of the EVs with the associated imaging agent, and wherein the imaging data is indicative of a bio-distribution of the homing agent from the spatial distribution of the EVs.

In some embodiments, at least one atom in the derivative of poly(ethylene glycol) or the phenothiazine derivative is associated with a biological targeting agent, and wherein the homing agent having the associated biological targeting agent target is homed, by the biological targeting agent, to a specific location of the subject, the biological targeting agent being at least one of a synthetic moiety, a protein, a peptide, an antibody, and a cell receptor molecule.

In some embodiments, the homing agent is the derivative of phenothiazine, wherein the derivative of phenothiazine is methylene blue, and wherein the amount of the homing agent administered is less than or equal to a ratio multiplied by the body mass of the subject, the ratio being 1000 nanograms of homing agent per 25 grams body mass of the subject.

In some embodiments, the ratio is a range of 100 to 1000 nanograms of homing agent per 25 grams body mass of the subject.

In some embodiments, the extracellular vesicles are naturally derived, having no chemical or biological modifications.

In some embodiments, the naturally derived extracellular vesicles are derived from a living organism.

In some embodiments, the extracellular vesicles are naturally derived having at least one chemical or biological modification.

In some embodiments, the method further includes: administering a homing agent at a second tissue site of the subject, the second tissue site being at a sufficient distance away from a first tissue site of the subject; imaging the second tissue site of the subject; and wherein the sufficient distance prevents an overlap between the generated image scenes of the first and the second tissue site.

In some embodiments, the amount of homing agent is associated with a matrix, wherein the matrix is selected from the group consisting of materials with a hydrophilic surface, materials with a charged surface, nucleic acids, proteins, lipids, ceramics, hydroxyapatite, tri-calcium phosphates, a component of an extracellular matrix, polymers, activated carbon particles, silicates, and combinations thereof.

In some embodiments, the matrix is at least one of a synthetic polymer, or a naturally occurring polymer; wherein the synthetic polymer is selected from the group consisting of:

polystyrene, poly-L-lactic acid, polyglycolic acid, poly-DL-lactic acid-co-glycolic acid, poly-D-lysine, polyamide, polyacrylamide, pyrrole, poly-pyrrole, and combinations thereof; and wherein the naturally occurring polymer is selected from the group consisting of: collagen, proteoglycans, fibrous proteins, silk, keratin, laminin, fibronectin, gelatin, agarose, agar, albumin, biofilms, alginate, polysaccharides, chitosan, cellulose, glycans, and combinations thereof.

Some embodiments of the disclosure provide a method for screening compounds for potential extracellular vesicles (EVs) homing capabilities, the method comprising: (a) administering a compound that has a potential for homing EVs to at least one of a subject, or an in vitro system; (b) administering EVs with an associated imaging agent to the at least one of the subject, or the in vitro system (c) imaging the EVs of the subject, or the in vitro system, with an imaging modality that corresponds with the imaging agent to determine if the compound that has a potential for homing EVs homes the administered EVs.

In some embodiments, the imaging agent is at least one of a radiation-emitter, a photon emitter, a fluorescent dye that emits light in a range of 400 nanometers to 1000 nanometers, a fluorescent peptide that emits light in the range, an ultrasonic contrast agent, or a magnetic resonance imaging contrast agent.

In some embodiments, at least one atom in the imaging agent is a positron emitter selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{211}At$, $^{75}Br$, $^{76}Br$, $^{82}Rb$, $^{43}Sc$, $^{44}Sc$, $^{86}Y$, $^{89}Zr$, $^{90}Nb$, $^{94m}Tc$, $^{110m}In$, $^{118}Sb$, and $^{124}I$.

In some embodiments, at least one atom in the imaging agent is a photon emitter selected from the group consisting of $^{67}Ga$, $^{99m}Tc$, $^{111}In$, $^{123}I$, $^{125}I$, $^{131}I$, and $^{201}Tl$.

In some embodiments, at least one atom in the imaging agent is a magnetic resonance imaging contrast agent selected from the group consisting of ions of gadolinium, manganese, and iron.

In some embodiments, the subject is at least one of an animal model, or a chick embryo model.

Some embodiments of the disclosure provide a method for treating or diagnosing a medical condition in a subject, the method comprising: (a) administering to the subject a homing agent at an administration site, wherein the homing agent is at least one of derivative of poly(ethylene glycol), or a derivative of phenothiazine; and (b) waiting a time sufficient to allow naturally occurring extracellular vesicles within the subject to accumulate at or near homing agent in the subject, and wherein the administration site is at least one of a tissue, a blood vessel, or a lymph vessel.

In some embodiments, the subject has a diseased tissue, the diseased tissue being at least one of a tumor, an inflammation, an injury, and an infection, wherein the diseased tissue produces disease derived extracellular vesicles within the subject, the method further comprising: homing of the disease derived extracellular vesicles to the homing agent in the subject, thereby disrupting disease-promoting actions of the disease derived extracellular vesicles in the subject either by preventing the disease derived extracellular vesicles from traveling to or traveling from the diseased site.

In some embodiments, the administration site is located in the diseased tissue.

In some embodiments, the administration site is different than the diseased tissue.

In some embodiments, the homing agent includes methylene blue.

In some embodiments, the method further includes removing a tissue or a bodily fluid of the subject that contains the accumulated naturally occurring extracellular vesicles.

In some embodiments, the tissue or the bodily fluid is removed at or near the administration site of the subject.

In some embodiments, the bodily fluid is at least one of blood, plasma, lymph, urine, sweat, or cerebrospinal fluid.

In some embodiments, the method further includes injecting healthy extracellular vesicles into the subject, and wherein injecting healthy extracellular vesicles occurs after the tissue or the bodily fluid has been removed.

In some embodiments, the healthy extracellular vesicles are at least one of extracellular vesicles derived from the subject, or naturally derived extracellular vesicles with no or at least one chemical or biological modification.

Some embodiments of the disclosure provide a method for diagnosing a medical condition in a subject, the method comprising: (a) removing a tissue or a bodily fluid from the subject; and (b) extracting extracellular vesicles from the bodily fluid or tissue by using particles that are associated with an extraction agent; wherein the extraction agent is at least one of derivative of poly(ethylene glycol), or phenothiazine.

In some embodiments, the bodily fluid is at least one of blood, plasma, lymph, urine, sweat, or cerebrospinal fluid.

In some embodiments, the subject is at least one of a patient, or an organism having patient derived diseased tissue, and wherein the organism is an animal.

Some embodiments of the disclosure provide a method for extracting EVs from a culture medium of living organisms or microorganisms, the method comprising: (a) removing a culture medium; and (b) extracting extracellular vesicles from the culture medium by using particles that are associated with an extraction agent; wherein the extraction agent is at least one of derivative of poly(ethylene glycol), or a phenothiazine derivative.

In some embodiments, the extraction agent includes methylene blue.

Some embodiments of the disclosure provide a method for treating a medical condition in a subject, the method comprising: (a) administering to the subject an amount of homing agent at an administration site, wherein the homing agent is at least one of a poly(ethylene glycol), or a derivative of phenothiazine; (b) administering to the subject extracellular vesicles, each of the extracellular vesicles being associated with a bioactive agent; and (c) waiting a time sufficient to allow the administered extracellular vesicles to home to the homing agent in the subject.

In some embodiments, the administration site includes a tumor, and wherein the bioactive agent includes a cytotoxic agent and/or a therapeutic agent.

In some embodiments, the cytotoxic agent is selected from the group of antitumor agents consisting of enzymes, carbohydrates, lipids, proteins, peptides, amino acids, peptides, miRNA, nucleic acids, drugs, antibodies, cell receptor molecules, biological response modifiers, a chemotherapeutic agent selected from the group consisting of: alkylating agents, antagonists, alkaloids, intercalating antibiotics, enzyme inhibitors, antimetabolites, mitotic inhibitors, growth factor inhibitors, cell cycle inhibitors, enzymes, biological response modifiers, and radiotherapy isotopes, and wherein the radiotherapy isotopes are selected from a group consisting of $^{213}Bi$, $^{223}Ra$, $^{177}Lu$, $^{225}Ac$, $^{212}Pb$, $^{211}At$, $^{166}Ho$, $^{89}Sr$, $^{153}Sm$, $^{105}Rh$, $^{125}I$, $^{131}I$, $^{90}Y$, $^{47}Sc$, $^{77}Br$, $^{67}Cu$, $^{149}Pr$, $^{199}Ag$, $^{149}Tb$, $^{161}Tb$, and $^{186}Re$, and combinations thereof.

In some embodiments, the administration site includes a diseased site, and wherein the bioactive agent includes a therapeutic agent.

In some embodiments, the therapeutic agent is selected from the group consisting of: antagonists, alkaloids, antibiotics, enzyme inhibitors, antimetabolites, growth factor inhibitors, enzymes, carbohydrates, lipids, proteins, peptides, amino acids, peptides, miRNA, nucleic acids, drugs, antibodies, cell receptor molecules, biological response modifiers, and combinations thereof.

In some embodiments, the bioactive agent is disposed within an enclosed volume of each of the extracellular vesicles.

In some embodiments, the bioactive agent is adsorbed to a portion of a surface of each of the extracellular vesicles.

In some embodiments, the bioactive agent is covalently bonded to a membrane protein that spans at least a portion of a lipid bilayer of each of the extracellular vesicles.

In some embodiments, step (a) administering to the subject an amount of homing agent at an administration site, wherein the homing agent is at least one of a poly(ethylene glycol), or a derivative of phenothiazine is repeated a plurality of times.

In some embodiments, step (c) waiting a time sufficient to allow the administered extracellular vesicles to home to the homing agent in the subject is repeated a plurality of times.

In some embodiments, the amount of homing agent is administered over a period of time, wherein the period of time is selected from the group consisting of a minute, an hour, a day, and combinations thereof.

In some embodiments, step (a) administering to the subject an amount of homing agent at an administration site, wherein the homing agent is at least one of a poly(ethylene glycol), or a derivative of phenothiazine is repeated a plurality of times, and step (b) administering to the subject extracellular vesicles, each of the extracellular vesicles being associated with a bioactive agent is repeated a plurality of times.

In some embodiments, the homing agent includes methylene blue.

Some embodiments of the disclosure provide a method for treating or diagnosing a medical condition in a subject, the method comprising: (a) administering to the subject an amount of a homing agent, wherein the homing agent is at least one of poly(ethylene glycol), or a derivative of phenothiazine, and wherein the homing agent includes an associated biological targeting agent defining a targeted homing agent, the biological targeting agent allowing targeting of the homing agent to a specific location within the subject; (b) waiting a time sufficient to allow the targeted homing agent to accumulate at the specific location within the subject, due to the biological targeting agent associated with the homing agent; and (c) waiting a time sufficient to allow naturally occurring extracellular vesicles (EVs) within the subject, or administered EVs to accumulate at the specific location of the subject, due to the homing of the extracellular vesicles to the homing agent of the targeted homing agent.

In some embodiments, the targeted homing agent includes methylene blue.

Some embodiments of the disclosure provide a method for treating or diagnosing a medical condition in a subject, the method comprising: (a) administering to the subject a homing agent, wherein the homing agent is at least one of derivative of poly(ethylene glycol), or a derivative of phenothiazine, and wherein the homing agent includes an associated biological targeting agent, the biological targeting agent allowing targeting of the homing agent to a specific location within the subject; (b) waiting a time sufficient to allow the targeted homing agent to accumulate at the specific location within the subject, due to the targeting moiety associated with the homing; (c) waiting a time sufficient to allow naturally occurring extracellular vesicles within the subject to accumulate at the specific location of the subject, due to the homing of the extracellular vesicles to the targeted homing agent.

In some embodiments, the targeted homing agent includes methylene blue.

Some embodiments of the disclosure provide a method for treating or diagnosing a medical condition in a subject, the method comprising: (a) administering to the subject a homing agent, wherein the homing agent is at least one of derivative of poly(ethylene glycol), or a derivative of phenothiazine, and wherein the homing agent includes an associated biological targeting agent defining a targeted homing agent, the biological targeting agent allowing targeting of the homing agent to a specific location within the subject; (b) administering to the subject extracellular vesicles, each of the extracellular vesicles being associated with a bioactive agent;_(c) waiting a time sufficient to allow the targeted homing agent to accumulate at the specific location within the subject, due to the biological targeting agent associated with the homing agent; (d) waiting a time sufficient to allow the administered extracellular vesicles to home to the specific location within the subject, due to the homing of the extracellular vesicles to the homing agent of the targeted homing agent.

In some embodiments, the targeted homing agent includes methylene blue.

Some embodiments of the disclosure provide a formulation for extracting extracellular vesicles, the formulation comprising: a plurality of beads; and a plurality of extraction agents associated with a given bead within the plurality of beads, and wherein when a solution containing extracellular vesicles is contacted with the plurality of beads, the extracellular vesicles home to the extraction agent.

In some embodiments, the plurality of extraction agents include at least one of a phenothiazine derivative, or a derivative of poly(ethylene glycol).

In some embodiments, the extracellular vesicles temporarily bind to the extraction agent.

In some embodiments, the extraction agents are covalently bonded to the given bead within the plurality of beads.

In some embodiments, the plurality of beads comprise a resin.

Some embodiments of the disclosure provide a compound comprising: a homing agent configured to home extracellular vesicles; and a biological targeting moiety associated to the homing agent.

Some embodiments of the disclosure provide a compound of formula (I):

(I)

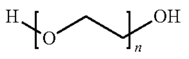

n = 3-45 and further comprising a biological targeting moiety associated therewith.

In some embodiments, the biological targeting moiety is covalently linked to at least one atom of the compound, and wherein the biological targeting moiety is a targeting peptide.

Some embodiments of the disclosure provide a compound of formula (II):

(II)

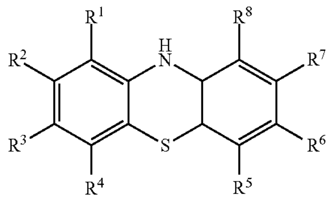

wherein each of $R^1$, $R^2$, $R^3$, $R^4$, $R^5$, $R^6$, $R^7$, and $R^8$ is independently an atom or a group of atoms, and further comprising a biological targeting moiety associated therewith.

In some embodiments, the biological targeting moiety is covalently linked to at least one atom of the compound, and wherein the biological targeting moiety is a targeting peptide.

Some embodiments of the disclosure provide a compound of formula (III):

(III)

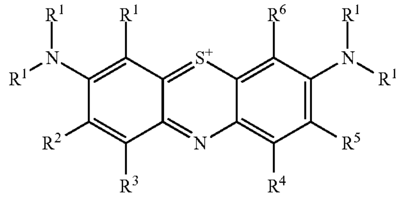

wherein each of $R^1$, $R^2$, $R^3$, $R^4$, $R^5$, $R^6$, $R^7$, and $R^8$ is independently an atom or a group of atoms, and further comprising a biological targeting moiety associated therewith.

In some embodiments, the biological targeting moiety is covalently linked to at least one atom of the compound, and wherein the biological targeting moiety is a targeting peptide.

DESCRIPTION OF THE DRAWINGS

The invention will be better understood, and features, aspects and advantages other than those set forth above will become apparent when consideration is given to the following detailed description thereof. Such detailed description makes reference to the following drawings.

DETAILED DESCRIPTION

Figure 1:
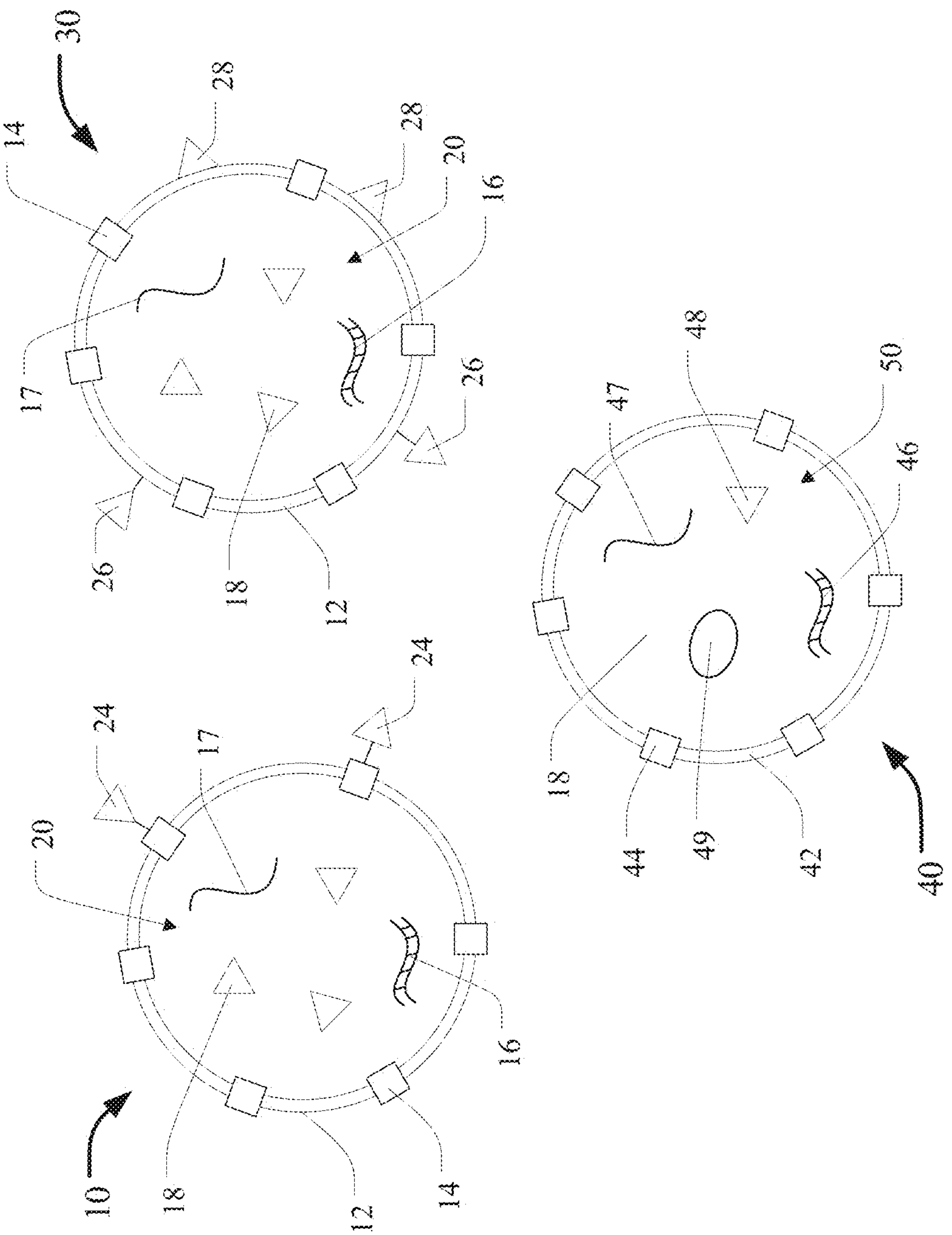
FIG. 1 shows an illustration of various extracellular vesicles, according to aspects of the present disclosure.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the use the phraseology and terminology used herein is for the purpose of description and should not be regarded as limiting. Furthermore, the use of "right", "left", "front", "back", "upper", "lower", "above", "below", "top", or "bottom" and variations thereof herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Unless otherwise specified or limited, phrases similar to "at least one of A, B, and C," "one or more of A, B, and C," and the like, are meant to indicate A, or B, or C, or any combination of A, B, and/or C, including combinations with multiple or single instances of A, B, and/or C.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. Skilled artisans will recognize the examples provided herein have many useful alternatives and fall within the scope of embodiments of the invention.

As used herein, the term "extracellular vesicles" broadly encompasses cell-derived vesicles. For example, "extracellular vesicles" can include exosomes, ectosomes, microvesicles, microparticles, macrovesicles, dexosomes, exosome like vesicles, exovesicles, nanovesicles, membrane particles, oncosomes, prominosomes, prostasomes, shedding microvesicles/vesicles, epididymosomes, archeosomes, tolerosomes, apoptotic bodies, budding vesicles, argosomes, blebbing vesicles, budding vesicles, extracellular membrane vesicles, membrane vesicles, etc. In some embodiments, the term "extracellular vesicles" can also include other artificial transport structures, such as liposomes, or micelles, where these artificial transport structures can include biological structures (e.g., lipids, proteins, amino acids, peptides, nucleic acids, carbohydrates, enzymes, RNA, mRNA, miRNA, DNA, metabolites, inorganic salts, cytoplasm, signaling molecules, transmembrane proteins, integral membrane proteins, cell receptors, etc.).

As used herein, the term "associated" describes the interaction between two atoms, molecules, biological structures, and combinations thereof. In some embodiments, this interaction can include physical or chemical interactions, or combinations of physical and chemical interactions. Physical interactions can include adsorption, absorption, intermolecular interactions, intramolecular interactions, van der Waals forces, electrostatic interactions, encapsulation, dipolar interactions, dipole-dipole interactions, dipole-induced dipole interactions, charge-dipole interactions, hydrogen bonding, magnetic dipole-dipole interactions, ligand interactions, coordination complexes, entrapment, etc. Chemical interactions can include covalent bonding, ionic bonding, indirect bonding (i.e., an atom or group of atoms that chemically links the two atoms, molecules, or biological structures together), etc.

As used herein, the term "naturally derived" describes the source of the substance. For example, "naturally derived" can refer to the lack of biological or chemical modifications to the specific substance. More specifically, in the context of "naturally derived extracellular vesicles" this can refer to the source of these extracellular vesicles being from living organisms (e.g., allogenic or autologous) or microorganisms but not limited to cultured cells, tissues, fungi, plant, animal, bacteria, etc. These, "naturally derived extracellular vesicles" further refer to the lack of biological or chemical modifications to the extracellular vesicles. In some embodiments, "naturally derived extracellular vesicles" does not refer to other atoms, chemicals, or biological structures that can be added with the "naturally derived extracellular vesicles" (e.g., a solvent, salts, bases, acids, etc.).

As used herein the term "bioactive agent" can include any atoms, groups of atoms, molecules, or biological structures (e.g., miRNAs, antibodies etc.) that provide a degree of therapy to a subject. In some cases, the bioactive agent specifically provides therapy to treat a specific disease state of a subject. In some embodiments, the specific disease state can be vascular disorders (e.g., atherosclerosis, aneurysms, arterial/venous stenosis, high blood pressure, arteriovenous malformation, peripheral artery disease, etc.) cardiac disorders (e.g., congestive heart failure, cardiomyopathies, ischemic heart disease, etc.) inflammatory diseases (e.g., chronic kidney disease, Crohn's, inflammatory bowel disease, chronic obstructive pulmonary disease, asthma, rheumatoid arthritis, etc.) regenerative therapies (e.g., for the heart, liver, pancreas, lung, etc.) metabolic disorders (e.g., obesity, diabetes, dyslipidemia, endocrine, etc.) traumatic disorders (e.g., traumatic brain injury, spinal cord injury, etc.), infections (e.g., fungal, bacterial, orthopedic implant associated, etc.), neurologic disorders (e.g., neurodegenerative diseases, Alzheimer's, Parkinson's, Huntington's, etc.) psychiatric disorders (e.g., attention-deficit/hyperactivity disorder, autism spectrum disorder, depression, etc.), immunology issues (e.g., immunotherapies, etc.), oncology (e.g., glioblastoma, prostate, breast, ovarian, pancreas, head/neck, lung, melanoma, osteosarcoma, etc.), transplants (e.g., liver, kidney, pancreas, heart, etc.), aging tissues, bone repair, antiviral therapies and combinations thereof. In some embodiments, the specific disease state can be chronic, acute, and can be single or multi-symptomatic. In some embodiments, the bioactive agent can include a cytotoxic agent. The cytotoxic agent can include a chemotherapeutic agent, radiotherapy isotopes such as $^{213}$Bi, $^{223}$Ra, $^{177}$Lu, $^{225}$Ac, $^{212}$Pb, $^{211}$At, $^{166}$Ho, $^{89}$Sr, $^{153}$Sm, $^{105}$Rh, $^{125}$I, $^{131}$I, $^{90}$Y, $^{47}$Sc, $^{77}$Br, $^{67}$Cu, $^{149}$Pr, $^{199}$Ag and $^{186}$Re, alkylating agents, antagonists, plant alkaloids, intercalating antibiotics, enzyme inhibitors, antimetabolites, mitotic inhibitors, growth factor inhibitors, cell cycle inhibitors, enzymes, biological response modifiers, and combinations thereof. In some embodiments, the bioactive agent can include other pharmaceuticals. In some embodiments, the bioactive agent can include DNA, RNA, or other gene(s), lipid(s), carbohydrate(s), protein(s), amino acid(s), peptide based therapeutics, etc., In some embodiments, the bioactive agent(s) are loaded or introduced to EVs by various physical methods but not limited permeabilization by detergents, electroporation, etc. or by engineering the parent cells to express the "bioactive agent" that will eventually go to the parent cell produced EVs.

As used herein the term "imaging agent" can include any atoms, groups of atoms, molecules, or biological structures that increase the visibility of a medical image. For example, an imaging agent can include a radiation-emitter, a fluorescent dye (e.g., emitting light at 400-1000 nm), a fluorescent peptide (e.g., emitting light at 400-1000 nm), an ultrasonic contrast agent, a magnetic resonance imaging contrast agent, a computed tomography contrast agent, X-ray contrast agent, and combinations thereof. In some embodiments, the imaging agent can include $^{11}$C, $^{13}$N, $^{15}$O, $^{18}$F, $^{34m}$Cl, $^{38}$K, $^{45}$Ti, $^{177}$Lu, $^{51}$Mn, $^{52m}$Mn, $^{212}$Pb, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{211}$At, $^{75}$Br, $^{76}$Br, $^{82}$Rb, $^{43}$Sc, $^{44}$Sc, $^{86}$Y, $^{90}$Y, $^{89}$Zr, $^{90}$Nb, $^{94m}$Tc, $^{110m}$In, $^{118}$Sb, and $^{124}$I.

In some embodiments, the imaging agent can include $^{67}$Ga, $^{99m}$Tc, $^{111}$In, $^{123}$I, $^{125}$I, $^{131}$I, and $^{201}$Tl. In some embodiments, the imaging agent can include ions of gadolinium, manganese, and iron. In some embodiments, the imaging agent can include other medical imaging contrast agents known in the art.

As used herein the term "homing agent" can include compounds configured to home extracellular vesicles. One example of a "homing agent" can be polymers such as poly(ethylene glycol), branched poly(ethylene glycol) or polypropylene oxide ("PPO") or polypropylene glycol ("PEG"), or derivatives thereof. In some embodiments, "homing agent" can include block copolymers including PEG, or block copolymers of PPO/PPG. In some embodiments, "homing agent" can include pluronics (e.g., poloxamers), which are triblock copolymers of PEO (hydrophilic), PPO (hydrophobic), arranged in an alternating structure of A-B-A, or more specifically, PEO-PPO-PEO. In some embodiments, the polymers can be branched in various different manners (e.g., being branched, or being linear), can have various chain lengths, can have various molecular weights, can have different end groups (e.g., the end group of the polymer not including a hydroxyl group), etc. In some embodiments, "homing agent" can include a derivative of poly(ethylene glycol), or a derivative of phenothiazine, or combinations thereof, configured to home extracellular vesicles. In some embodiments, the homing agent can include derivatives of poly(ethylene glycol) consisting of Formula I, below. The poly(ethylene glycol) could range from 150 to 2000 Daltons. In some cases, the poly(ethylene glycol) of Formula I can have repeating units of 3-45 (e.g., n=3-45, below). In other words, each ethylene substructure having two carbon molecules multiplied by the repeating unit (e.g., n below) can determine the total number of carbon molecules for a given molecule of poly(ethylene glycol). In some cases, the poly(ethylene glycol) can be branched, while in other cases, the poly(ethylene glycol) can be linear. The poly(ethylene glycol) could also have different end groups (e.g., end groups other than hydroxyl groups). In some embodiments, "homing agent" can include poly(ethylene glycol) ("PEG") with varying chain lengths, branching, PEG/PPO containing copolymers, which in some cases, can be potentially useful in homing (attracting) extracellular vesicles (e.g., exosomes).

In some embodiments, "homing agent" can include polymers described in non-patent literature reference, "Design and Biocatalytic Synthesis of Pluronics-based Nanomicellar Self-assembly Systems for Drug Encapsulation Applications" ("Pandey, et al"), in non-patent literature reference, "Design and Synthesis of Novel Pegylated 4-Methylcoumarins" ("Pandey, et al.-1"), in non-patent literature reference, "Design, synthesis and anti-inflammatory evaluation of PEGylated 4-methyl and 4,8-dimethylcoumarins" ("Pandey, et al.-2"), in non-patent literature reference, "Biocatalytic Approach for the Synthesis of Glycerol-Based Macroamphiphiles and their Self-Assembly to Micellar Nanotransporters" ("Gupta, et al."), in non-patent literature reference, "Design, synthesis and evaluation of novel PEGylated curcumin analogs as potent Nrf2 activators in human bronchial epithelial cells" ("Pandey, et al.-3"), and non-patent literature reference, "Design and synthesis of perfluorinated amphiphilic copolymers: Smart nanomicelles for theranostic applications" ("Pandey, et al.-4"), all of these references are hereby incorporated by reference herein in their entirety for all purposes.

In some embodiments, the "homing agent" is the compound of formula (I) below, or derivatives thereof.

(I)

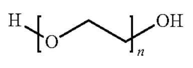

n = 3-45

In some embodiments, with regard to the "homing agents" described above that are polymers, the branching of the polymers can be important so as to adjust (increase or decrease) the lipophilicity of the polymer, which can alter the solubility of the polymer. Additionally, the length of the polymer chains can be adjusted to also adjust (increase or decrease) the solubility of the polymer. In some cases, these characteristics of the polymer can be altered to modify the homing ability of the polymer.

In some embodiments, the phenothiazine derivatives can include methylene blue. In some embodiments, the homing agent is selected from a group consisting of Formula (II), a tautomer of Formula (II), a stereoisomer of Formula (II), a salt of Formula (II), and combinations thereof, where Formula (II) is:

(II)

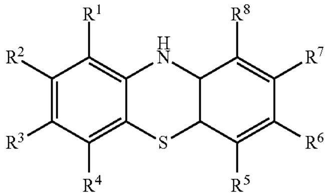

and each of $R^1$, $R^2$, $R^3$, $R^4$, $R^5$, $R^6$, $R^7$, and $R^8$ is independently an atom or a group of atoms. In some embodiments, with regard to Formula (I), $R^1$, $R^2$, $R^3$, $R^4$, $R^5$, $R^6$, $R^7$, and $R^8$ can be independently selected from a group consisting of hydrogen, substituted or unsubstituted alkyl, substituted or unsubstituted alkyl carbonyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, OH, halogen, substituted or unsubstituted alkoxy, substituted or unsubstituted amino, and substituted or unsubstituted carboxylate. In some embodiments, with regard to Formula (I and II), at least one atom can be replaced with a positron emitter selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{211}At$, $^{75}Br$, $^{76}Br$, $^{82}Rb$, $^{43}Sc$, $^{44}Sc$, $^{86}Y$, $^{89}Zr$, $^{90}Nb$, $^{94m}Tc$, $^{110m}In$, $^{118}Sb$, and $^{124}I$. In some embodiments, with regard to Formula (I and II), at least one atom can be replaced with a photon emitter selected from the group consisting of $^{67}Ga$, $^{99m}Tc$, $^{111}In$, $^{123}I$, $^{125}I$, $^{131}I$, and $^{201}Tl$. In some embodiments, with regard to Formula (I and II), at least one atom can be replaced with a magnetic resonance imaging contrast agent selected from the group consisting of ions of gadolinium, manganese, and iron. In some embodiments, Formula (I and II) can be associated with a bioactive agent. In some embodiments, the homing agent is selected from a group consisting of Formula (III), a tautomer of Formula (III), a stereoisomer of Formula (III), a salt of Formula (III), and combinations thereof, where Formula (III) is:

(III)

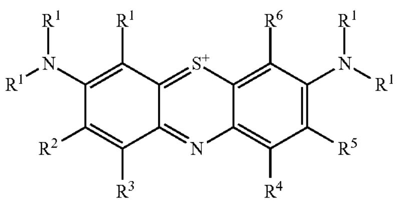

and each of $R^1$, $R^2$, $R^3$, $R^4$, $R^5$, $R^6$, $R^7$, and $R^8$ is independently an atom or a group of atoms. In some embodiments, with regard to Formula (III), $R^1$, $R^2$, $R^3$, $R^4$, $R^5$, $R^6$, $R^7$, and $R^8$ can be independently selected from a group consisting of hydrogen, substituted or unsubstituted alkyl, substituted or unsubstituted alkyl carbonyl, substituted or unsubstituted alkenyl, substituted or unsubstituted alkynyl, substituted or unsubstituted cycloalkyl, substituted or unsubstituted heterocycloalkyl, substituted or unsubstituted aryl, heteroaryl, OH, halogen, substituted or unsubstituted alkoxy, substituted or unsubstituted amino, and substituted or unsubstituted carboxylate. In some embodiments, with regard to Formula (III), at least one atom can be replaced with a positron emitter selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{211}At$, $^{75}Br$, $^{76}Br$, $^{82}Rb$, $^{43}Sc$, $^{44}Sc$, $^{86}Y$, $^{89}Zr$, $^{90}Nb$, $^{94m}Tc$, $^{110m}In$, $^{118}Sb$, and $^{124}I$. In some embodiments, with regard to Formula (III), at least one atom can be replaced with a photon emitter selected from the group consisting of $^{67}Ga$, $^{99m}Tc$, $^{111}In$, $^{123}I$, $^{125}I$, $^{131}I$, and $^{201}Tl$. In some embodiments, with regard to Formula (III), at least one atom can be replaced with a magnetic resonance imaging contrast agent selected from the group consisting of ions of gadolinium, manganese, and iron. In some embodiments, Formula (III) can be associated with a bioactive agent.

As used herein, the term "chemicals/chemical libraries" can include any atoms, groups of atoms, molecules, or biological structures that is hypothesized to home extracellular vesicles. For example the chemicals/chemical libraries can include but not limited to molecular rings, similar to those that appear in phenothiazine (e.g., benzene groups, heterocyclic compounds, etc.).

As used herein, the term "targeted homing agent" can include any biological or synthetic structure, moiety, etc., that is homed to a specific portion in the subject. For example, the term "targeted homing moiety" can include various homing peptides as one example.

As used herein, the term "therapeutic agent" can include any molecule, or groups of molecules intended to provide a particular level of therapy. For example, a therapeutic agent can include antagonists, alkaloids, antibiotics, enzyme inhibitors, antimetabolites, growth factor inhibitors, enzymes, carbohydrates, lipids, proteins, peptides, amino acids, peptides, miRNA, nucleic acids, drugs, antibodies, cell receptor molecules, biological response modifiers, combinations thereof, etc.

EVs are essential for many functions in the body, including cell signaling (or other communications) between various biological entities (e.g., between organs, etc.). Thus, due to the great importance of EVs in the body, it is not surprising that EVs have been utilized across various research fields to study possible new treatments, or to uncover new diagnosis pathways. As described above, currently EVs have been engineered with targeting peptides (e.g., on the surface of a given EV) aimed to direct the EVs to travel to the intended location (as intended by the targeting peptide, and targeting structure, such as an organ). However, although in theory these engineered EVs should be able to home to the intended location, the homing ability is not foolproof. In fact, the homing effectiveness, and therapeutic effectiveness of these engineered EVs is currently unknown.

Thus, the study of new EV related treatments (or therapies), diagnosing pathways, and generally the understanding of EVs (e.g., communication pathways) have been largely a trial and error iterative process, being passive and observational. For example, for EV related therapies, EVs are engineered, or captured, and re-injected (systemically or locally) with the hope that some of the EVs will either travel to the intended location in the case of systemic injection, or in the case of local injection refrain from traveling, and rather stay near the local injection site. As another example, typical EV related diagnostics rely on the natural abundance of the EVs in the body (e.g., tissues, urine, biological fluids, etc.) for identifying disease specific markers. Thus, in some cases, the amount of EVs collected in a sample are too few in number to supply the necessary amount of markers. This requires the practitioner to acquire additional samples, which may or may not fulfill the required amount of disease specific markers. In other words, the unpredictable nature of being tied to the natural abundance of the EVs in the body, such as a sample, can be undesirable.

Some embodiments of the disclosure provide improvements over typical EV related diagnostics, therapies, etc., and others, by providing homing of EVs to a desired location with a homing agent. For example, the homing agent can be injected in vivo (or placed in vitro), which draws or homes the EVs to the location of the homing agent. In some embodiments, the homing agent can include poly(ethylene glycol), polypropylene oxide, polypropylene glycol, and derivatives thereof, or a derivative of phenothiazine. In some embodiments, the derivative of phenothiazine can be methylene blue. This homing property has far reaching applications across various methods, systems, etc., related to EVs, and offers significant advantages over prior systems, and methods.

In some embodiments, the homing agent may have additional modifications comprising Streptavidin-biotin system or other affinity based binding systems that will further enhance binding of the homed EVs and prolong the retention of homed EVs at the homing agent (e.g., the injection site of the homing agent).

In some embodiments, on-demand homing of native or bioactive agent carrying extracellular vesicles without chemical or biological modifications or target enrichment would be a major advancement in extracellular vesicle, research, diagnostics, and related therapeutics. No current systems exist for in vivo homing of unmodified extracellular vesicles (e.g., natural extracellular vesicles without chemical or biological modifications) to a target site.

In some embodiments, the present disclosure provides the homing of unmodified or therapeutic carrying extracellular vesicles to a target tissue for therapeutic treatment. In some embodiments, the therapeutic payloads may include drugs, radiotherapy isotopes, other previously described agents (therapeutic molecules, chemicals, structures) or combinations thereof.

In some embodiments, the present disclosure provides the elevation of levels of extracellular vesicles in biological fluids including but not limited to blood, plasma, lymph, urine, sweat, cerebrospinal fluid, for enhancement of diagnostic sensitivity of liquid biopsies.

In some embodiments, the present disclosure provides in vitro purification or enrichment of extracellular vesicles using resins/beads derivatized with phenothiazine or poly (ethylene glycol).

In some embodiments, the present disclosure derivative of poly(ethylene glycol), or a derivative of phenothiazine that can be used to interact with specific extracellular vesicles in vivo and in vitro. For the in vivo application, this can be a way to disrupt communication of primary tumor niches, pre-metastatic niches, post-metastatic niches, or combinations of niches. For the in vitro application, this can be a way to isolate specific extracellular vesicles.

In some embodiments, the present disclosure provides derivative of poly(ethylene glycol), or a derivative of phenothiazine with biological targeting moieties, which can be used to redirect extracellular vesicles to selective tissues in the body.

In some embodiments, the present disclosure provides different doses or time or site of administration of derivative of poly(ethylene glycol), or a derivative of phenothiazine, which can modulate extracellular vesicle based interventions.

In some embodiments, the present disclosure provides the use of a labeled derivative of poly(ethylene glycol), or a derivative of phenothiazine, for imaging and identifying distribution of extracellular vesicles in the body. In some embodiments, this information in the context of normal or diseased patients can help us better understand the role of extracellular vesicles in both normal and disease processes, enabling the tailoring of specific treatment methodologies.

In some embodiments, the present disclosure provides a derivative of poly(ethylene glycol), or a derivative of phenothiazine, which can be used to perform mechanistic studies to understand the mechanism by which extracellular vesicles from one established cancer site can contribute to establishment of pre-metastatic niches and overall dysfunction of the immune system. This can allow for tailoring of specific treatment methodologies.

In some embodiments, the present disclosure provides extracellular vesicle-homing compounds, which can include but are not limited to a derivative of poly(ethylene glycol), or a derivative of phenothiazine. In some embodiments, the derivative of poly(ethylene glycol), or the derivative of phenothiazine can serve as a positive control or reference compound in order to screen other chemicals/chemical libraries with extracellular vesicle-homing capabilities. As described in more detail below, the present in vivo animal model system can be used, or alternatively, a chick embryo chorioallantoic membrane in vivo model, or other in vitro extracellular vesicle-homing model systems can be used. In some cases, the extracellular vesicles under study can be radiolabeled with PET or single-photon emission computed tomography ("SPECT") probes. Additionally or alternatively, the extracellular vesicles can be tagged with fluorescent dyes/peptides (e.g., emitting light at 400-1000 nm), MRI contrast agents, or ultrasound-based probes.

In some embodiments, the present disclosure provides extracellular vesicle-homing compounds, which can include but are not limited to phenothiazine (and derivatives), or glycol (polyethylene glycols) compounds that can be covalently or non-covalently adsorbed to an immobilized matrix at the target tissue site. In this case, the matrix allows for the concentration of these extracellular vesicle-homing compounds to be relatively constant at the site for homing extracellular vesicles. Further, these immobilized matrices can be mixtures of materials, which can include but is not limited to materials with hydrophilic surfaces, materials with charged surfaces, nucleic acids, proteins, lipids, ceramics (e.g., hydroxyapatite, tri-calcium phosphate, etc.), components of the extracellular matrix, synthetic polymers (e.g., polystyrene, poly-L-lactic acids, polyglycolic acids, poly-DL-lactic acid-co-glycolic acids, poly-D-lysines, Geltrex™ reduced growth factor basement membrane matrix, fibronectin-collagen (FNC), polyamides, polyacrylamides, pyrroles (e.g., doped, or undoped), poly-pyrroles (e.g., doped or undoped)) or natural polymers (e.g., collagens, proteoglycans, fibrous proteins, silks, keratins, laminins, fibronectins, gelatins, agaroses, agars, albumins, biofilms, polysaccharide like alginates, chitosans, celluloses, glycans, etc.), activated carbon, silicates, or other EV-homing compound adsorbents.

In some embodiments, the present disclosure provides varying administration sites of the free or immobilized extracellular vesicle-homing compounds, which can include but is not limited to intravenous, intra-arterial, intraperitoneal, in lymph system, within tissue, extracellular space, adventitia, implants, subcutaneous, or dermal patch administration regions.

In some embodiments, the present disclosure provides reconditioning of the various extracellular vesicle populations within the blood and tissues of a subject by extracting specific circulating extracellular vesicle population(s) using derivatized extracellular vesicle-homing compounds for chronic conditions. In some embodiments, the chronic conditions can include sleep apnea, obesity, diabetes, partial remission stage of cancer, etc.

FIG. 1 illustrates examples of extracellular vesicles, according to various embodiments of the present disclosure. For example, FIG. 1 shows an extracellular vesicle 10 that includes a membrane 12 and membrane proteins 14, where each membrane protein 14 spans at least a portion of the thickness of the membrane 12. As illustrated, the membrane 12 is a lipid bilayer with spaced apart membrane proteins 14. Although, membrane proteins 14 are illustrated as fixed, at least some of the membrane proteins 14 can readily translate along the circumference of the membrane 12. In some embodiments, the extracellular vesicle 10 does not contain membrane proteins 14, while in other embodiments, the membrane 12 can be a single layer. The extracellular vesicle 10 also includes associated bioactive agents 18, 24. The bioactive agent 18 is depicted as residing within the enclosed volume 20 of the extracellular vesicle 10, where the enclosed volume 20 is defined by the membrane 12. Also residing within the enclosed volume 20 are DNA and RNA fragments 16, 17. In some embodiments, the extracellular vesicle does not contain either DNA fragments 16, RNA fragments 17, or both. The extracellular vesicle 10 also includes bioactive agents 24 which are associated with a corresponding membrane protein 14. The association between the bioactive agent 24 and the membrane protein 14 is illustrated as being a covalent linkage, although other associations as described above are possible. In some embodiments, the bioactive agents 18, 24 can be substituted for an imaging agent. In other embodiments, the extracellular vesicle 10 can be naturally derived (e.g., containing no biological or chemical modifications) and then modified to include the associated bioactive agents/imaging agents.

FIG. 1 also illustrates an extracellular vesicle 30 that includes similar structures as described above with regard to the extracellular vesicle 10. For example, the extracellular vesicle is depicted as having a membrane 12, membrane proteins 14, and associated bioactive agents 18 disposed within the enclosed volume 20 of the extracellular vesicle 30. The extracellular vesicle 30 also includes DNA and RNA fragments 16, 17. In some embodiments, the extracellular vesicle does not contain either DNA fragments 16, RNA fragments 17, or both. The extracellular vesicle 30 is further depicted to include associated bioactive agents 26, 28. The bioactive agent 26 is shown as covalently linked to the membrane 12, while the bioactive agent 28 is shown as being adsorbed to a surface of the membrane 12 (e.g., via electrostatic attraction). In some embodiments, the bioactive agents 26, 28 can be substituted for imaging agents. In other embodiments, the extracellular vesicle 30 can be naturally derived and modified to include the associated bioactive agents/imaging agents.

FIG. 1 is further illustrated to include a naturally derived extracellular vesicle 40. As described above, the naturally derived extracellular vesicle 40 is not chemically or biologically modified, and is derived from an organism or microorganisms including but not limited to cultured cells/tissues/animal/plant/fungi/bacteria etc. Similarly to the extracellular vesicles 10, 30, the naturally derived extracellular vesicle 40 includes a membrane 42 and membrane proteins 44, where each membrane protein 44 spans at least a portion of the thickness of the membrane 42. As illustrated, the membrane 42 is a lipid bilayer with spaced apart membrane proteins 44, although in alternative embodiments the membrane 42 can be a single layer. Although, membrane proteins 44 are illustrated as fixed, at least some of the membrane proteins 44 can readily translate along the circumference of the membrane 42. In some embodiments, the naturally derived extracellular vesicle 40 does not contain membrane proteins 44. The naturally derived extracellular vesicle 40 also includes a DNA fragment 46, an RNA fragment 47, a bioactive agent 48, and an imaging agent 49 all disposed within the enclosed volume 50 of the naturally derived extracellular vesicle 40, where the membrane 42 defines the enclosed volume 50. In some embodiments, the bioactive agent 48 and the imaging agent 49 can be associated with the extracellular vesicle 40, as described above with the term associated (e.g., adsorbed to a surface of the membrane 42, covalently bonded to the membrane proteins 44, etc.).

Figure 2:
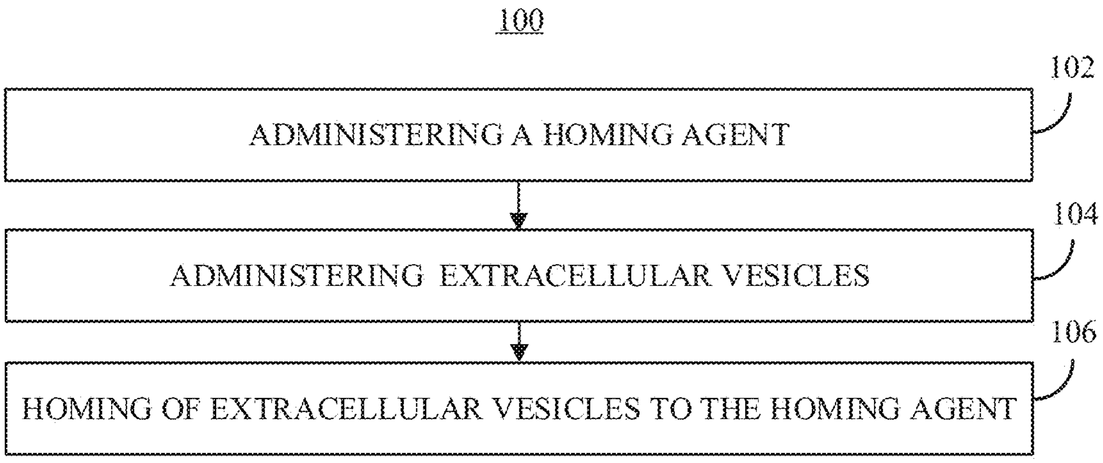
FIG. 2 shows a flowchart of a process for treating medical condition of a subject with homing of extracellular vesicles to a homing agent.

FIG. 2 illustrates a flowchart of a process 100 for treating a medical condition of a subject by homing therapeutic extracellular vesicles to the diseased site. The process involves homing of the extracellular vesicles to a desired site with the homing agent. In one aspect of the disclosure, an inherent property of the homing agent (e.g., a derivative of phenothiazine methylene blue, a derivative of poly(ethylene glycol)) allows extracellular vesicles to home to the tissue where the homing agent was administered. Thus, extracellular vesicles within the subject, which includes the extracellular vesicles independent of origin, will be homed to any desired location where the homing agent was administered.

At 102, the process 100 includes administration of the homing agent to a desired site including but not limited to a diseased site (e.g., a cancerous site). In some embodiments, the homing agent can be injected into a subject (e.g., via a syringe) at a particular location of the subject. In some embodiments, the particular location can be a blood vessel, a muscle site, a tissue site, a lymph site, a cancerous tissue (e.g., a tumor), etc. The bio-distribution of the homing agent can be dependent on a number of factors including but not limited to the dosage given, the size and structure of the homing agent, perfusion of the tissue, and the location where the homing agent was administered to the subject.

At 104, the process 100 includes administering the therapeutic extracellular vesicles. In some embodiments, the extracellular vesicles are similar to those described above, with regard to FIG. 1 (e.g., natural extracellular vesicles 10, 30 with modifications, and naturally derived extracellular vesicles 40). In some embodiments, the extracellular vesicles are naturally derived extracellular vesicles, having no chemical or biological modifications. In other specific embodiments, the extracellular vesicles are derived from the subject being imaged (e.g., via extraction of extracellular vesicles from a bodily fluid of the subject). In some embodiments, the therapeutic extracellular vesicles can be injected into a subject (e.g., via a syringe) at a particular location of the subject. In some embodiments, the particular location can be a blood vessel, muscle site, tissue site, lymph site, etc.

At 106, the process includes homing of the administered extracellular vesicles to or near the site where homing agent was administered. As described above, the extracellular vesicles are homed (e.g., by an inherent property of the extracellular vesicles and the homing agent) to or near the homing agent (e.g., at or near the administration site). In other words, the extracellular vesicles are driven to (or near) the location the homing agent (e.g., such as where the homing agent was administered). This homing property is particularly advantageous at least because the EVs are ensured to travel, migrate, home, etc., to the location of the homing agent. This way, the payload on a particular EV (e.g., such as a cytotoxic agent, other drug, etc.) can be sure to interact where the homing agent is located (e.g., the cytotoxic agent being delivered to a cancerous site).

Although the process 100 is illustrated as having a specific order, the process 100 need not be completed in any particular order. For example, in some embodiments, the administering of the extracellular vesicles (e.g., at 104) can be completed before the administering of the homing agent (e.g., at 102).

Figure 3:
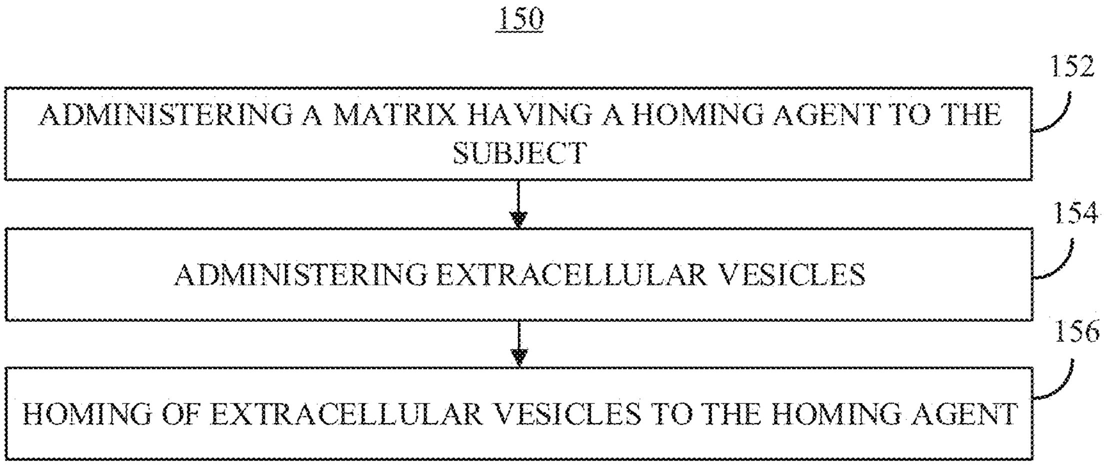
FIG. 3 shows a flowchart of a process for treating a medical condition of a subject by homing extracellular vesicles to a homing agent in a matrix.

FIG. 3 illustrates a flowchart of a process 150 for treating a medical condition of a subject by homing therapeutic extracellular vesicles to a site (e.g., a diseased site). At 152, process 150 includes administering a matrix having a homing agent to a subject. For example, a matrix (e.g., a hydrogel, Geltrex™, etc.) can be modified to include the homing agent. More specifically, the homing agent can be associated (e.g., covalently, electrostatically, etc.) with the matrix so as to prevent migration of the homing agent (by a particular amount) away from the matrix. In some cases, covalent bonding of the homing agent to the matrix is desirable at least because it immobilizes the homing agent (e.g., movement of the homing agent relative to the matrix is restricted). After association of the homing agent to the matrix, the matrix can be implanted in the subject at a desired location (e.g., a tumor site, etc.).

At 154, process 150 includes administering extracellular vesicles to the subject, such as, and similar to 104 of process 100. For example, in some embodiments, the extracellular vesicles are similar to those described above, with regard to FIG. 1 (e.g., natural extracellular vesicles 10, 30 with modifications, and naturally derived extracellular vesicles 40). In some embodiments, the extracellular vesicles are naturally derived extracellular vesicles, having no chemical or biological modifications. In other specific embodiments, the extracellular vesicles are derived from the subject being imaged (e.g., via extraction of extracellular vesicles from a bodily fluid of the subject). In some embodiments, the therapeutic extracellular vesicles can be injected into a subject (e.g., via a syringe) at a particular location of the subject. In some embodiments, the particular location can be a blood vessel, muscle site, tissue site, lymph site, etc.

At 156, process 150 includes homing of the extracellular vesicles to the homing agent associated with the matrix, such as and similar to 106 of process 100. In some embodiments, the extracellular vesicles are driven, homed, etc., to the desired site with the homing agent associated with (e.g., immobilized in) the matrix. In some embodiments, the distribution of the homing agent is restricted to the matrix. Thus, extracellular vesicles within the subject, which includes the extracellular vesicles independent of origin (e.g., extracellular vesicles that are in the subject but have not been injected), will be homed to any desired location where the having an associated (immobilized) homing agent was administered.

Figure 4:
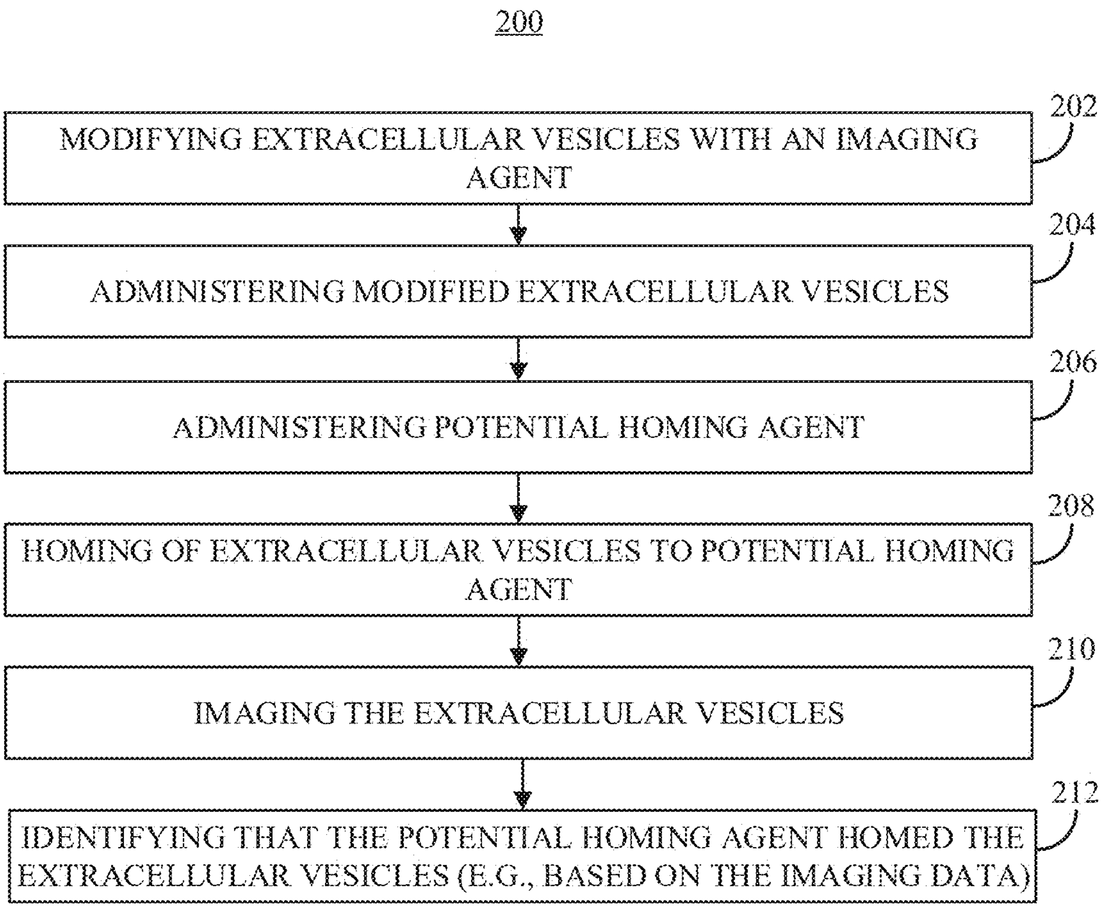
FIG. 4 shows a flowchart of a process for screening potential extracellular vesicle homing agents.

FIG. 4 illustrates a flowchart of a process 200 for screening potential extracellular vesicle homing agents using individual compounds or compounds from a library (e.g., a chemical library). At step 202, process 200 includes labeling or modifying extracellular vesicles with an imaging agent. For example, as previously described, the imaging agent can correspond to many different imaging modalities (e.g., ultrasound, computed tomography, x-ray, MRI, PET, etc.), and the imaging agent can be associated with the extracellular vesicles in many different ways (e.g., covalently bonded, electrostatically associated, located within the internal volume of the extracellular vesicle, etc.). Similarly, the extracellular vesicles can be derived from the subject (e.g., which may mitigate any immunological responses), or can be derived from other organisms.

At 204, process 204 includes administering the imaging agent modified extracellular vesicles. In some embodiments, the modified extracellular vesicles can be injected into a subject (e.g., via a syringe) at a particular location of the subject (e.g., similar to 154 of process 150, and 104 of process 100). In some embodiments, the particular location can be any tissue, blood vessel, muscle site, lymph site, etc. Alternatively, the modified extracellular vesicles can be administered in an ex vivo scenario. For example, the modified extracellular vesicles can be administered into a central location within a fluid conduit, or in some cases, the extracellular vesicles can be administered into a well, where two wells are in fluid communication with the fluid conduit.

At 206, process 200 includes administering compounds as a potential extracellular vesicle homing agent. In some embodiments, the compounds can be injected into a subject (e.g., via a syringe) at a particular location of the subject. In some embodiments, the particular location can be any tissue, a blood vessel, muscle site, lymph site, etc., and can be different than the location of the injected extracellular vesicles. Alternatively, the potential extracellular vesicle homing agent compounds can be administered in an ex vivo scenario. For example, the potential homing agent can be administered into a central location within a fluid conduit, into a well, where two wells are in fluid communication with the fluid conduit. In some embodiments, the administration location of the extracellular vesicles is different than the administration location of the potential homing agent, so as to prevent any possible false positive results.

At 208, process 200 includes the homing of the extracellular vesicles to a compound with homing capability. If the potential homing compound has a homing capability (or a degree) of homing the extracellular vesicles will be drawn, homed, etc., to the potential homing compound.

At 210, the process 200 includes imaging the extracellular vesicles with an imaging modality. In some embodiments, the imaging modality corresponds to the imaging agent. For example, the imaging agent can be gadolinium and the imaging modality can be magnetic resonance imaging ("MRI"), or the imaging agent can be a PET radioisotope and the imaging modality can be PET imaging, or the imaging agent can be a fluorescence probe (e.g., emitting light having a wavelength of 400-1000 nm) and the imaging can be optical imaging. Imaging the extracellular vesicles allows for viewing of the modified extracellular vesicles within the specific in vivo or in vitro scenario. Specifically, imaging of the extracellular vesicles introduced into the subject, or imaging the extracellular vesicles introduced in the in vitro system, determines whether the test compound effectively homes the extracellular vesicles, and if so, a degree of homing. For example, a specific appearance in the image (or acquired imaging data) of the accumulation of extracellular vesicles near the test compound with homing capability determines that the test compound homes extracellular vesicles. As a more specific example, the number of extracellular vesicles accumulated by the test compound, and the distance each extracellular vesicle is to the test compound (and the distance relative to the extracellular administration site), can determine a degree of homing. The degree of homing can be compared to a threshold value, such as the positive control being a polyethylene derivative, or a phenothiazine derivative (e.g., methylene blue). Additionally, the comparison of image intensities between the test compounds can determine the degree to which each composition homes the extracellular vesicles. Further, to determine a the test compounds, the homing agent (derivatives of phenothiazine and poly(ethylene glycol)) can be used as a standard for a degree of homing, which can be used as an index for comparing other test compounds.

At 212, process 200 includes determining that the potential homing agent homed the extracellular vesicles, based on the imaging data. As described above, the number of extracellular vesicles near and their corresponding distances to the potential homing agent (such as near the administration site of the potential homing agent) can be deduced. In other cases, the image intensity from an acquired image (or imaging data) of the extracellular vesicles can be compared to the image intensity of the positive control (e.g., using derivatives of phenothiazine, or poly(ethylene glycol)). These can determinations can be used and compared to a threshold value (e.g., from the positive control) to determine if the potential homing agent is, in fact, a homing agent.

In some cases, process 200 can include determining the degree of homing between different homing agents. For example, in some cases, after extracellular vesicles have been added to an in vitro system, one confirmed homing agent at a first amount (e.g., a phenothiazine derivative) can be added to one side of the in vitro system (e.g., a first well), and another confirmed homing agent (e.g., determined after 212 of process 200) at a second amount (the same as the first amount) can be added to an opposing side (e.g., a second well) of the in vitro system. Then, after a period of time, the extracellular vesicles can be imaged (e.g., such as at 210 of process 200), which can determine the relative strength of homing between different homing agents, such as by the imaging quality. For example, more extracellular vesicles residing near the one confirmed homing agent as compared to the another confirmed homing agent can determine that the one confirmed homing agent has a greater (relative) degree of homing than the another confirmed homing agent. Additionally, one type of confirmed homing agent, and amount of confirmed homing agent, can be used as the relative standard.

Although the process 200 is illustrated as having a specific order, the process 200 need not be completed in any particular order. For example, the administering of the modified extracellular vesicles (e.g., at 204) can be completed after the administering of the homing agent (e.g., at 206).

Figure 5:
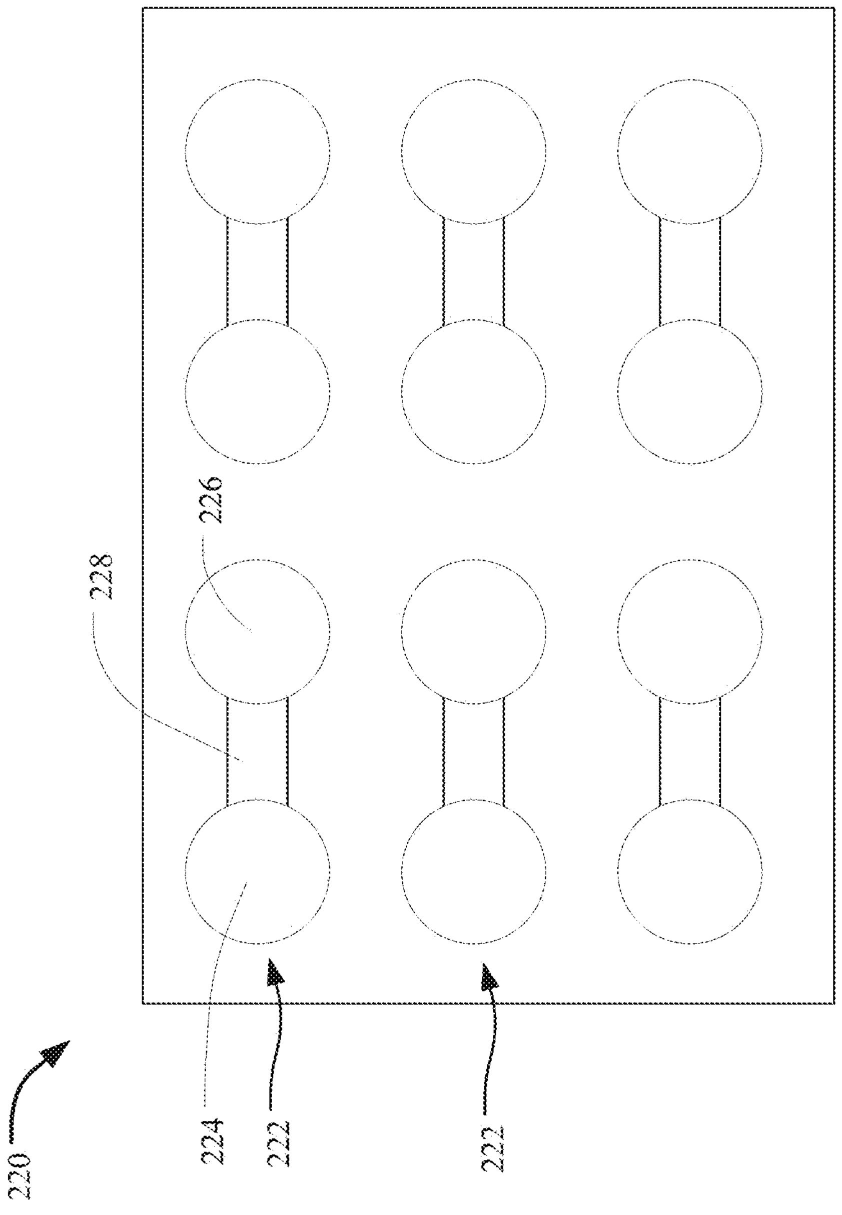
FIG. 5 shows an illustration of a substrate, which can be used to implement portions of the process of FIG. 4.

FIG. 5 shows an example of a substrate 220, which can be used to implement the process 200 of FIG. 4 to greatly increase throughput for screening potential extracellular vesicle homing agents. The substrate 220 includes a plurality of testing regions 222 each having wells 224, 226 joined together by a conduit 228. As shown, the wells 224, 226 and the conduit 228 are all in fluid communication with each other. With regard to the process 200, different homing agents can be tested in each of the testing regions 222 individually. For example, one region 222 can be tested as the positive control, another region 222 can be tested as a negative control (e.g., ionized water), and the remaining regions 222 can be tested for the potential homing agents that home extracellular vesicles. More specifically, with regard to testing within a particular testing region 222, the extracellular vesicles can be administered within the conduit 228, and the homing compound (or potential homing compound) can be administered within either of the wells 224, 226. In some cases, such as with testing the relative homing strength of one homing compound relative to another, the extracellular vesicles can be administered within the conduit 228, and one homing compound can be administered in the first well 224 (e.g., a phenothiazine derivative), and the other homing compound can be administered in the second well 226. In this case, the one homing compound can be administered in the first wells 224 for all of the testing regions 222, such that the relative strength for the other homing compounds remains consistent.

Figure 6:
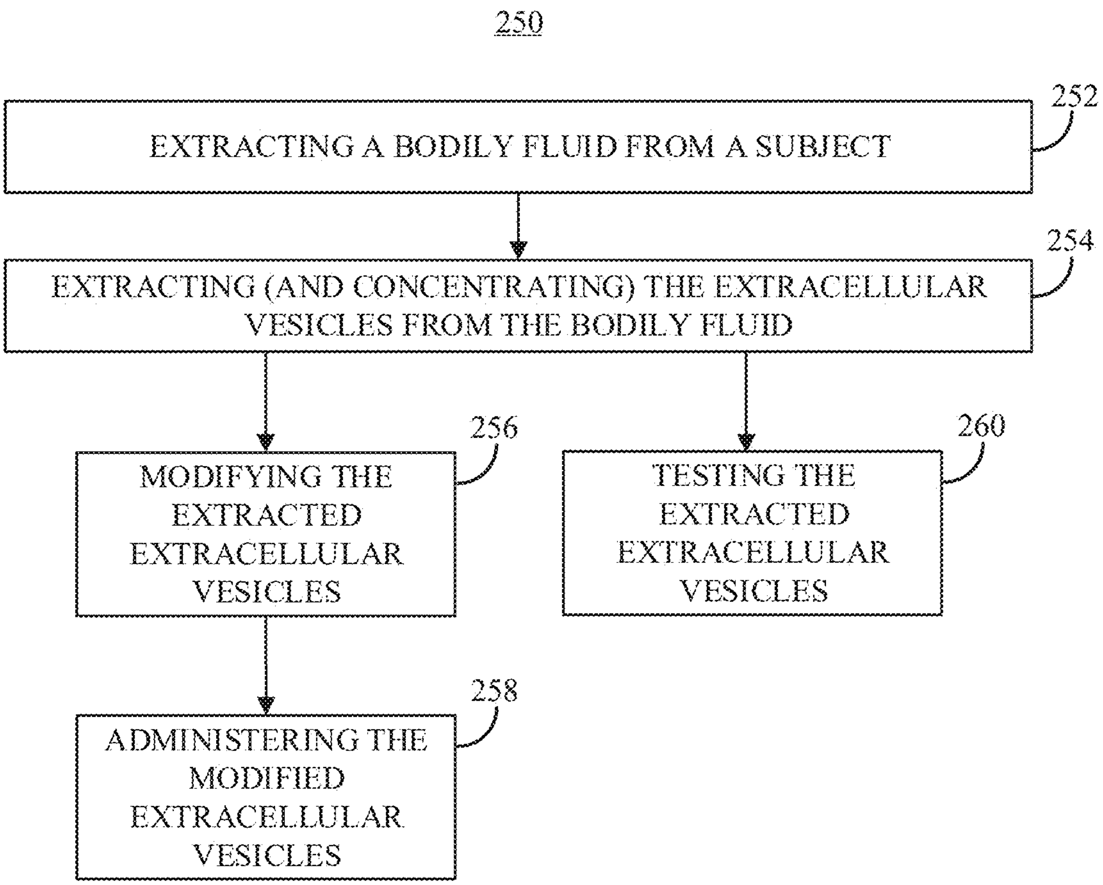
FIG. 6 shows a flowchart of a process for extracting extracellular vesicles from a body fluid of a subject.

FIG. 6 illustrates a flowchart of a process 250 for extracting extracellular vesicles from a bodily fluid. At 252, process 250 includes extracting a bodily fluid from a subject (e.g., via a syringe). In some embodiments, the bodily fluid can be at an easily accessible tissue site (e.g., a blood vessel, spinal tap, bladder, etc.). In some embodiments, the bodily fluid can be blood, plasma, lymph, urine, sweat, or cerebrospinal fluid.

Following extraction of bodily fluid, at 254 process 250 includes extracting the extracellular vesicles contained in the bodily fluid. In some embodiments, the harvested bodily fluid can be introduced to the extraction agent (e.g., the previously described homing agents) associated with or to the beads/resin. For example, the extraction reagent can be a derivative of phenothiazine or a derivative of poly(ethylene glycol). The bodily fluid can then be flushed with a solvent to elute everything but the extracellular vesicles, as the extracellular vesicles are homed to the extraction agent associated to the beads/resin. Then, a compound, solution, etc. can be added to the extracellular vesicles and extraction agent associated bead/resin mixture to elute the extracellular vesicles into a separate container, effectively increasing the concentration and purity of the extracellular vesicles.

At 256, process 250 can include modifying the extracted (and concentrated) extracellular vesicles. For example, the extracellular vesicles can be modified with a bioactive agent (as previously described, such as associating the bioactive agent with an extracellular vesicle), with an imaging agent, etc. At 258, process 258 can include administering the modified extracellular vesicles to a subject. In some cases, the subject that had the extracellular vesicles extracted is the same subject that receives the administered modified extracellular vesicles. This way, a potential treatment plan is tailored to the subject, as the extracellular vesicles administered to the subject are derived from the subject (which can decrease any undesirable immune response).

Additionally or alternatively, at 260 process 250 can include testing the extracted extracellular vesicles to diagnose a particular disease state. For example, the extracted extracellular vesicles can be tested for a particular biomarker indicative of (or corresponding to) a particular disease state (e.g., after centrifuging the extracted extracellular vesicles).

Figure 7:
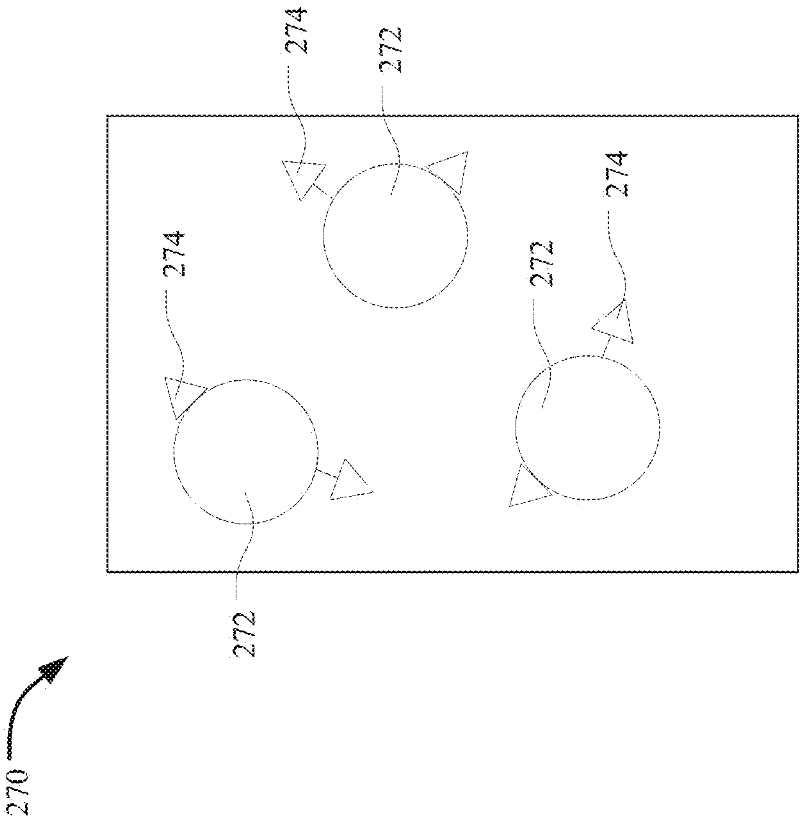
FIG. 7 shows an illustration of a column having a plurality of beads with associated extraction agents, which can be used to implement portions of the process of FIG. 6.

FIG. 7 shows an example of a column 270, which can be used to implement the process 250 of FIG. 6. The column 270 includes a plurality of beads 272 having associated extraction agents 274, which can include any previously described homing agent, or discovered homing agent (e.g., such as discovered from the process 200). The beads 272 can be formed of a suitable size, shape, etc., and can be formed out of various materials (e.g., polymers, resins, etc.). FIG. 7 shows various association schemes between the extraction agents 274 and the beads 272, such as covalently linked, and electrostatically linked. However, in alternative embodiments, other association schemes are contemplated. In some embodiments, the plurality of beads 272 are particles.

Figure 8:
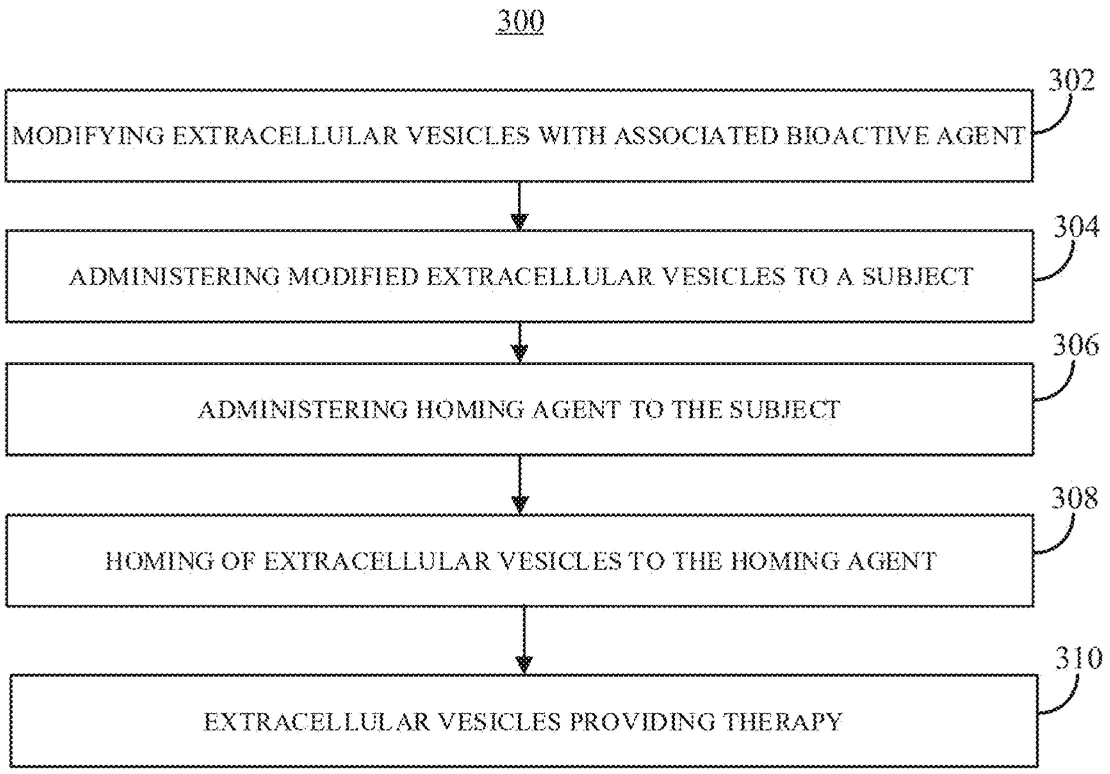
FIG. 8 shows a flowchart of a process for treating a medical condition of a subject with homing of extracellular vesicles associated with a bioactive agent.

FIG. 8 illustrates a flowchart of a process 300 for treating a medical condition of a subject. At step 302, process 300 includes modifying extracellular vesicles with a bioactive agent to create extracellular vesicles having an associated bioactive agent. In some embodiments, the extracellular vesicles are similar to those described above, with regard to FIG. 1 (e.g., extracellular vesicles 10, 20, and naturally derived extracellular vesicles 40 that have been associated with a bioactive agent). In some embodiments, the extracellular vesicles are derived from the subject being treated. In some embodiments, the extracellular vesicles can be derived from a cancerous site of the subject (e.g., a tumor). In some embodiments, the extracellular vesicles can be derived from an organism or microorganisms (including but not limited to cultured cells/tissues/animal/plant/fungi/bacteria etc.). In some embodiments, it may be advantageous to associate bioactive agents with naturally derived extracellular vesicles from a human, or more specifically, associate bioactive agents with naturally derived extracellular vesicles from the subject being treated. In both these cases, and particularly the subject derived extracellular vesicles case, once these are administered to the subject, as will be described below, the reaction/response from the subject's immune system will be decreased. For example, the subject's immune system will not recognize the extracellular vesicles as foreign invaders, and thus the immune system's response to the extracellular vesicles will be limited. Regardless of the source of the extracellular vesicles, the extracellular vesicles are associated with a bioactive agent to create extracellular vesicles having associated bioactive agent.

At 304, process 300 includes administering the bioactive associated extracellular vesicles. In some embodiments, the bioactive associated extracellular vesicles can be injected into a subject (e.g., via a syringe) at a particular location of the subject. In some embodiments, the particular location can be any tissue, a blood vessel, muscle site, lymph site, etc.

At 306, process 300 includes administering the homing agent. In some embodiments, the homing agent can be injected into a subject (e.g., via a syringe) at a particular location of the subject. In some embodiments, the particular location can be any tissue, a blood vessel, muscle site, lymph site, etc.).

At 308, process 300 includes homing of the bioactive associated extracellular vesicles to the homing agent. In some embodiments, an inherent property of the homing agent (e.g., a derivative of phenothiazine or poly(ethylene glycol)) allows extracellular vesicles to home to the homing agent. Thus, extracellular vesicles within the subject, which includes the modified extracellular vesicles, will be homed to the location of the homing agent.

At 310, process 300 includes providing therapy to the subject by the bioactive associated extracellular vesicles. As described in the previous step (e.g., at 308), the bioactive associated extracellular vesicles accumulate and home to the homing agent. Thus, because the bioactive associated extracellular vesicles are closer to their intended treatment site (e.g., if step 306 is administered to the treatment site), the bioactive agent can then treat the afflicted treatment site. For example, the bioactive associated extracellular vesicles can increase/decrease cell signal transduction, increase/decrease binding of cell receptor sites, unload contents (e.g., bioactive agents) from within the enclosed volume of the bioactive associated extracellular vesicles. These actions can all provide therapy for a disease state of the subject. In some embodiments, the bioactive agent corresponds to the afflicted treatment site (e.g., where the bioactive agent is a tissue plasminogen activator and the treatment site is a blood clot occluded blood vessel).

Figure 9:
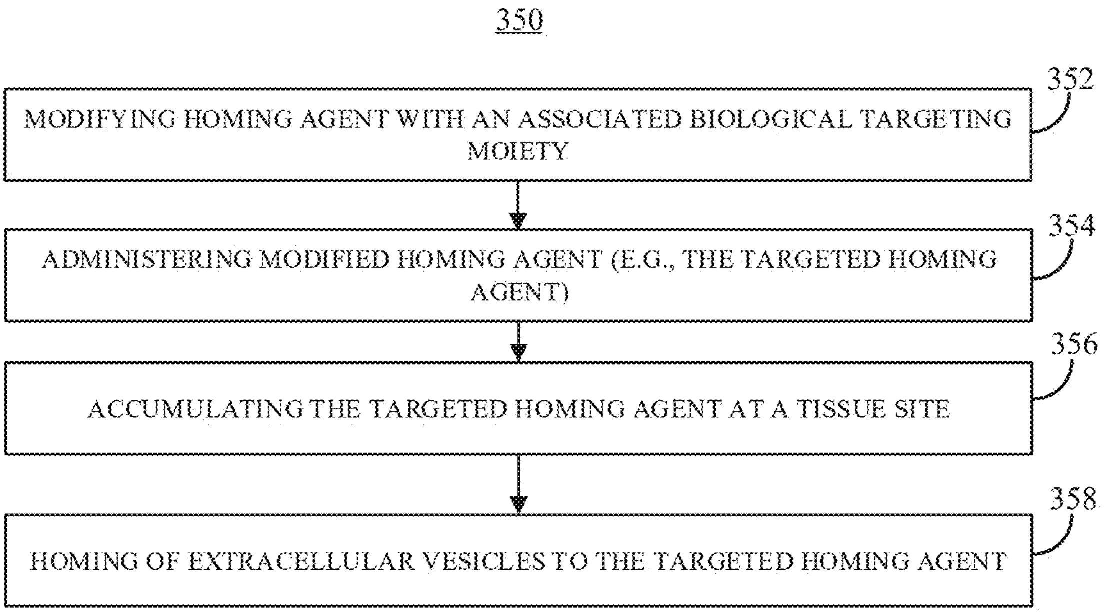
FIG. 9 shows a flowchart of a process for treating a medical condition of a subject by using a homing agent modified having a biologically targeting moiety.

FIG. 9 illustrates a flowchart of a process 350 for treating a medical condition of a subject. At 352, process 350 includes modifying the homing agent with a targeting moiety. In some embodiments, the targeting moiety is a homing peptide, where the homing peptide targets a particular region within a subject. In some embodiments, the homing agent is modified by associating a biological targeting moiety (e.g., a homing peptide) with the homing agent. In some specific embodiments, the biological moiety can be covalently linked to the homing agent (e.g., where one of the R groups of the previous formulations include a biological targeting moiety).

At 354, process 350 includes administering the modified homing agent that includes the targeting agent (e.g., the targeted homing agent). In some embodiments, the modified homing agent can be injected into a subject (e.g., via a syringe) at a particular location of the subject. In some embodiments, the particular location can be a blood vessel, muscle site, lymph site, etc.).

At 356, process 350 includes accumulating the modified homing agent at a tissue site (e.g., via the targeting agent associated with the homing agent). Due to the association of the biological targeting moiety, the modified homing agent will accumulate at a tissue site, which the targeting moiety is configured to be homed to, such as the liver, heart, lungs, etc. In other words, the biological targeting moiety, which is associated with the homing agent, will be homed (or forced to travel to) to the tissue site that is intended to receive the biological target moiety (e.g., a receptor site of a particular cell type). Thus, the targeted homing agent will be homed to the tissue site.

At 358, process 350 includes homing of the extracellular vesicles to the homing agent. An inherent property of the homing agent (e.g., a derivative of phenothiazine derivative or derivative of poly(ethylene glycol)) allows the extracellular vesicles to home to the homing agent. Thus, extracellular vesicles within the subject, will be attracted to the location of the accumulated homing agent, which has been homed to the tissue site where the targeting moiety has been targeted to (e.g., the liver, heart, lungs, etc.).

Figure 10:
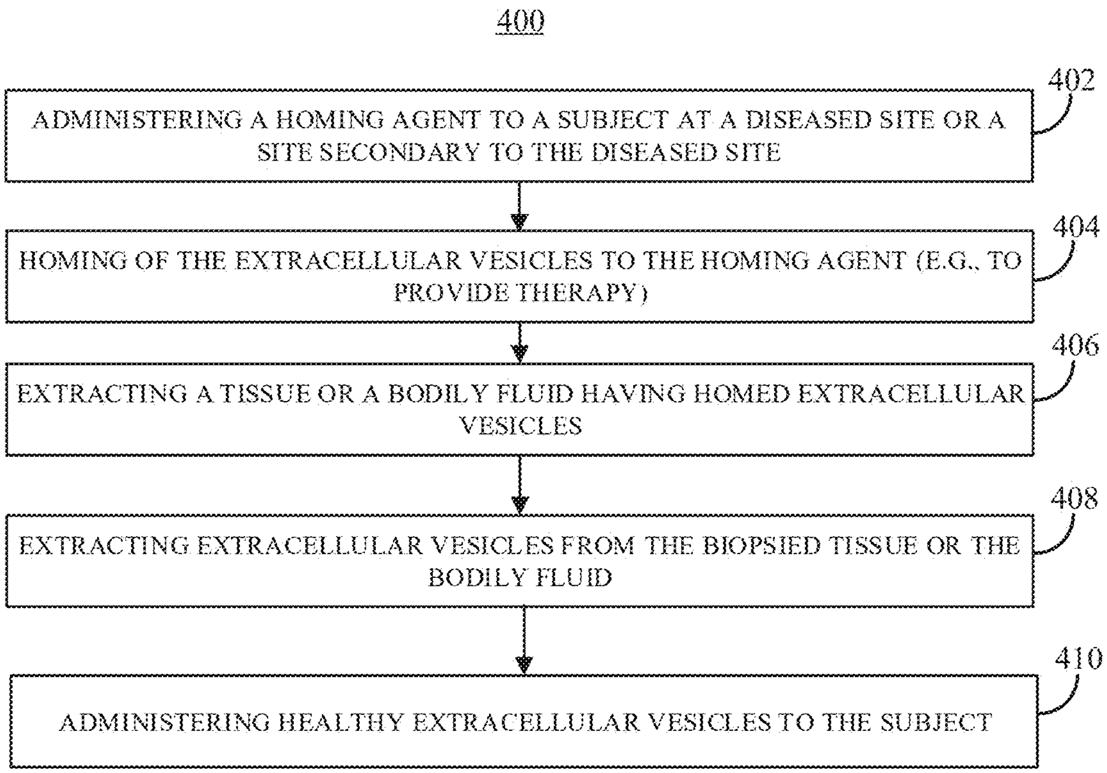
FIG. 10 shows a flowchart of a process for treating a medical condition of a subject.

FIG. 10 illustrates a flowchart of a process 400 for homing and extracting extracellular vesicles. At 402, process 400 includes administering a homing agent to a subject at a diseased site, or secondary to a diseased site. In some cases, the diseased site may be a tumor site. In some cases, the secondary site may be a blood vessel, which can provide relatively easy access to inject the homing agent, and later extract a bodily fluid (e.g., blood) containing extracellular vesicles from this site.

At 404, process 400 includes homing of extracellular vesicles to the homing agent. As described above, an inherent property of the homing agent (e.g., a derivative of phenothiazine or derivative of polyethylene glycol) allows extracellular vesicles to be homed (or drawn) to the homing agent. Thus, extracellular vesicles already present within the subject will be homed to the homing agent. In some cases, the extracellular vesicles already present in the subject can be derived from a diseased site (e.g., derived from a cancerous site).

In some embodiments, extracellular vesicles (from within the subject) once homed to the homing agent, can provide therapy. For example, in some embodiments, such as when the homing agent has been administered to a diseased site, and the extracellular vesicles having been homed to the homing agent (and thus have been homed to the diseased site), in some cases, the mere accumulation of extracellular vesicles (naturally produced in the subject) provides a degree of therapy for the subject, such as at the diseased site (e.g., via increased/decreased signal transduction, increased/decreased binding of cell receptor sites, or unloading of contents within the enclosed volume of the naturally derived extracellular vesicles). Thus, the homing of the natural extracellular vesicles already present within the subject by the homing agent at a location within the subject, provides therapy to that location. Additionally or alternatively, in some embodiments, process 400 at 404 can include homing of cancerous extracellular vesicles (e.g., extracellular vesicles derived from cancerous tissues) within the subject to the homing agent. This accumulation of cancerous extracellular vesicles effectively controls where the cancerous extracellular vesicles reside in a subject. Thus, this can prevent secondary cancerous sites from forming elsewhere in the subject. In some embodiments, once the cancerous extracellular vesicles within the subject accumulate at the homing agent, the cancerous extracellular vesicles can be extracted, such as at 406 of process 400 (e.g., via removal of a bodily fluid), which can prevent the formation of secondary cancer sites because at least some of the cancerous extracellular vesicles have been removed.

At 406, process 400 includes extracting a bodily fluid, or a tissue from a subject. In some embodiments, the type of bodily fluid (or tissue) extracted and the location of the extraction depends on where the homing agent was administered. For example, if the homing agent was administered into and accumulated in the muscle tissue, the extracellular vesicles would be homed to the muscle tissue site. Thus, step 406 would include extraction of a bodily tissue at the muscle tissue site. In some embodiments, the location where the homing agent was administered is the same location where the bodily fluid is extracted from.

At 408, process 400 includes extracting extracellular vesicles from the bodily fluid or the biopsied tissue. However, this step may be omitted due to the increased concentration of extracellular vesicles already present in the extracted sample, due to the accumulation of the extracellular vesicles within the subject at the homing agent accumulation site. Thus, the bodily fluid likely has enough extracellular vesicles in order to perform a diagnostic test that requires a certain amount of extracellular vesicles. However, in the case the extracellular vesicles need to be purified further (e.g., to provide a lab or manufacturer with extracellular vesicles), block 408 of process 400 can be completed. For example, at 408 process 400 can also include providing an extraction agent associated to beads or resins (e.g., within a column), such as the previously described column 270. The bodily fluid (or biopsied material being prepared accordingly), containing the extracellular vesicles, can be introduced to the extraction agent associated beads/resin. The bodily fluid can then be flushed with a solvent to elute everything but the extracellular vesicles, as the extracellular vesicles are homed to the extraction agent associated to the beads/resin. Then, a compound, solution, etc. can be added to the column having the extracellular vesicles and extraction agent associated bead/resin mixture, to elute the extracellular vesicles into a separate container, effectively increasing the concentration and purity of the extracellular vesicles. These purified/increased concentration extracellular vesicles can then be used to manufacture bioactive agent associated extracellular vesicles, as detailed above, or can be used to diagnose a particular disease state, as also detailed above.

At 410, process 400 includes administering extracellular vesicles to the subject. After the bodily fluid has been removed, which contains the accumulated extracellular vesicles, block 410 can be completed. Thus, block 408 is not required to complete block 410. The administering of extracellular vesicles can include any number and type of extracellular vesicles as previously described (e.g., naturally derived, or associated extracellular vesicles). In some embodiments, the removal of the bodily fluid that contains accumulated extracellular vesicles (e.g., block 406) can effectively remove unhealthy extracellular vesicles (e.g., cancer derived, or disease state related extracellular vesicles). Further, administering extracellular vesicles from healthy subjects or therapeutic extracellular vesicles back to the patient at block 410 can effectively "re-populate" extracellular vesicles within the subject. For example, "re-populate" extracellular vesicles implies altering a ratio of unhealthy extracellular vesicles to healthy extracellular vesicles, by increasing the amount of healthy extracellular vesicles (and in some cases decreasing the amount of unhealthy extracellular vesicles). In some embodiments, "healthy extracellular vesicles" implies extracellular vesicles that are not unhealthy extracellular vesicles.

Although processes 100, 150, 200, 250, 300, 350, and 400 have been described in a particular order, other steps within specific processes can be completed in other orders. Similarly, other steps from separate processes can be added to other processes. For example, step 210 can be added to processes 100, 150, 300 and 350 (granted at least the extracellular vesicle or homing agents with an associated biological targeting moiety also include imaging agents).

In some embodiments, any step within any process can be completed any number of times.

EXAMPLE

The following examples have been presented in order to further illustrate aspects of the disclosure, and are not meant to limit the scope of the disclosure in any way.

We have developed a novel method of homing extracellular vesicles to a desired site in the body via an onsite administration of either a derivative of phenothiazine (e.g., methylene blue), or poly(ethylene glycols) (e.g., a polyethylene glycol having a molecular weight of 400 with no endcap). In some embodiments, the poly(ethylene glycol) can have molecular weights other than 400, and can have other end groups. In some embodiments, other poly(ethylene glycols) are possible. This technology can be useful in homing both labeled and unlabeled extracellular vesicles for diagnosis and therapeutic applications, which can have far reaching effects on both extracellular vesicle based therapeutics and diagnostics.

We have discovered that non-toxic doses of phenothiazine derivatives or polyethylene glycols are useful for the homing of exogenous extracellular vesicles to specific tissues in the body. This discovery has many potential applications in therapy and diagnosis in its ability to spatially concentrate extracellular vesicles. These methods can improve the homing of extracellular vesicles to diseased tissues, as well as enriched sampling and extraction of extracellular vesicles for diagnostics at low cost. Rather than using extensively modified extracellular vesicles (e.g., with biological and/or chemical modifications), which can be complex and costly, extracellular vesicles can be targeted by using little to no modification of the extracellular vesicles themselves. This can have the potential to provide significantly less complex/expensive treatments using extracellular vesicles, as the lack of modification of the extracellular vesicles requires far less regulatory hurdles. Our initial findings show broad applicability with regard to the extracellular vesicles type/source and the target tissue in the context of homing using phenothiazine derivatives or polyethylene glycols. At present, the homing is effective with as low as 500 ng (1.6 nmol) of methylene blue injected at the target site. In this example, the target site is the subcutaneous area in foot pad of a mouse, with good perfusion of the methylene blue, so the effective amount of methylene blue for extracellular vesicle homing could be much lower than 500 ng (1.6 nmol).

Figure 11:
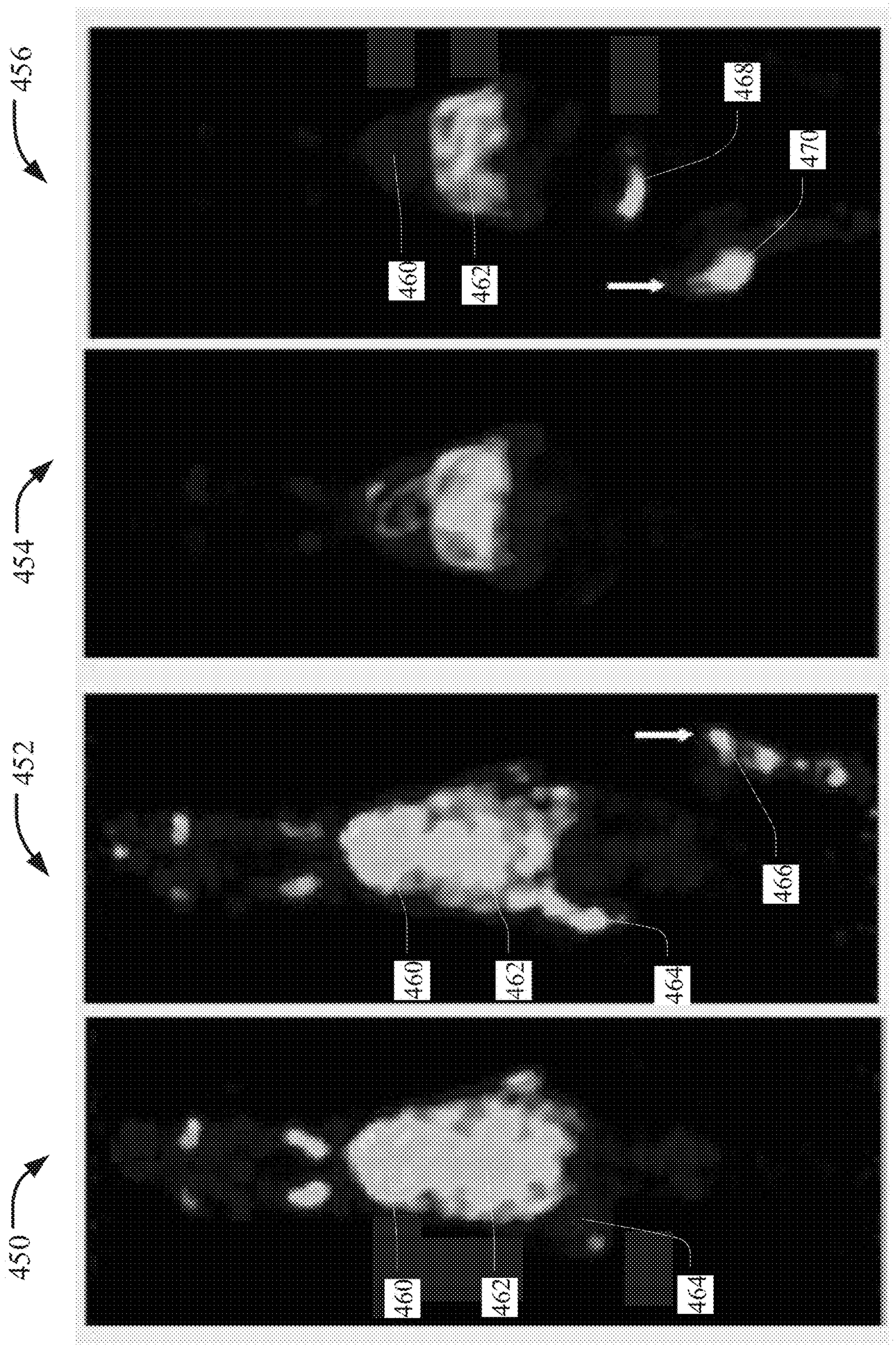
FIG. 11 shows positron emission tomography ("PET") images of an experiment using injected radiolabeled exosomes derived from stem cells and PC-3 prostate cancer cells, and also using a derivative of phenothiazine, methylene blue.

FIG. 11 illustrates four PET images of injected $^{89}Zr$ labeled exosomes in mice. PET images 450, 452 utilized stem cell derived exosomes, whereas PET images 454,456 illustrate prostate cancer (PC-3) derived exosomes. Both groups of exosomes were labeled with $^{89}Zr$, a positron emitter, which allows the exosomes to be tracked within the mouse by PET imaging. As illustrated in some or all of the PET images 450, 452, 454, 456, the heart/lungs 460, the liver 462, the gut 464/468 and 466/470 show "hotspots" of the $^{89}Zr$ labeled exosomes (homing agent mediated accumulation zones of the $^{89}Zr$ labeled exosomes). PET image 450 is a control (e.g., did not receive methylene blue), and was taken one hour after the mouse was intravenously injected (via tail vein) with the $^{89}Zr$ labeled stem cell derived exosomes. For PET image 452, the $^{89}Zr$ labeled stem cell derived exosomes were intravenously injected (via tail vein). Then after one hour, 1% methylene blue (in Lactated Ringer's Solution) was injected in a hind limb paw. The opposite hind limb paw received a methylene blue-free and sterile Lactated Ringer's Solution. One hour after administering the methylene blue solution, the PET image 452 was taken. As illustrated in the PET image 452, the hind paw that received the methylene blue injection, indicated by the reference numeral 466, shows a significant accumulation of the $^{89}Zr$ labeled stem cell derived exosomes. Conversely, the opposite paw, which received the methylene blue-free Lactated Ringer's Solution, did not show an accumulation of the $^{89}Zr$ labeled stem cell derived exosomes. Thus, the methylene blue homed the $^{89}Zr$ linked stem cell derived exosomes from circulation, effectively showing that the $^{89}Zr$ labeled stem cell derived exosomes targeted methylene blue.

Similarly to PET image 450, PET image 454 was taken one hour after the mouse was injected with the $^{89}Zr$ labeled PC-3 derived exosomes, and functioned as a control (e.g., did not receive methylene blue). For PET image 456, the $^{89}Zr$ labeled PC-3 derived exosomes were intravenously injected (via tail vein). Then after one hour, 1% methylene blue (in Lactated Ringer's Solution) was injected in a hind limb paw. The opposite hind limb paw received a methylene blue-free and sterile Lactated Ringer's Solution. One hour after administering the methylene blue solution, the PET image 456 was taken. As illustrated in the PET image 456, the hind paw that received the methylene blue injection, indicated by the reference numeral 470, shows a significant accumulation of the $^{89}Zr$ labeled PC-3 derived exosomes. Conversely, the opposite paw, which received the methylene blue-free Lactated Ringer's Solution, did not show an accumulation of the $^{89}Zr$ labeled PC-3 derived exosomes. Thus, methylene blue homed the $^{89}Zr$ labeled PC-3 derived exosomes from circulation to the paw region, effectively showing that the $^{89}Zr$ labeled PC-3 derived exosomes targeted methylene blue. For PET images 450, 454, neither of the hind paws in each image show any significant accumulation of $^{89}Zr$ labeled exosomes. Additionally, all PET images 450,452,454,456 show that methylene blue homes both stem cell and cancer derived exosomes.

Figure 12:
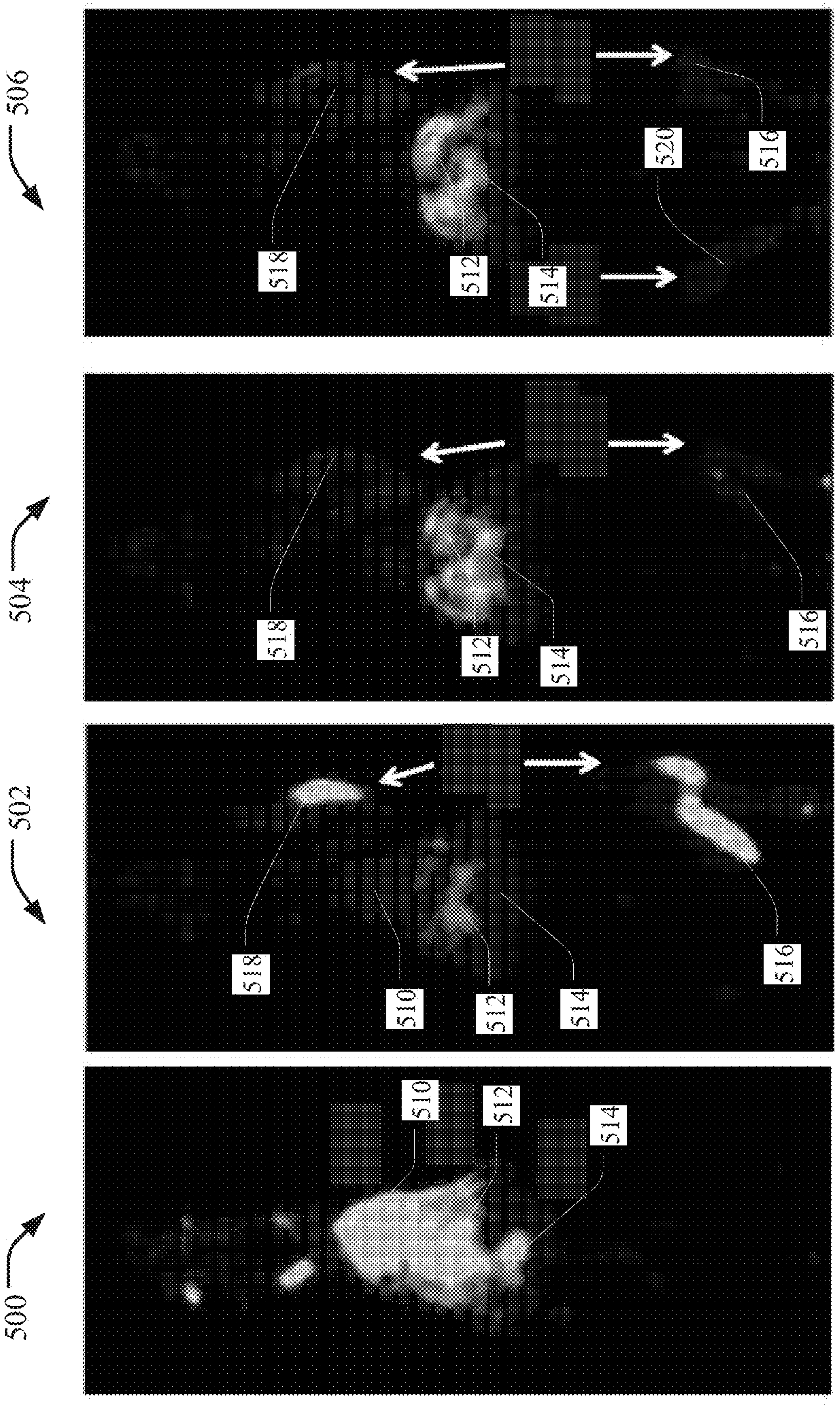
FIG. 12 illustrates four time-lapse PET images showing the bio-distribution of injected radiolabeled exosomes derived from stem cells, based on an injected derivative of phenothiazine, methylene blue.

FIG. 12 illustrates four time-lapse PET images showing the bio-distribution of injected $^{89}Zr$ labeled stem cell derived exosomes in a mouse. Similarly to the experiment illustrated in FIG. 11, stem cell derived exosomes were labeled with $^{89}Zr$, a positron emitter, which allows the exosomes to be tracked within the mouse by PET imaging. Then, the $^{89}Zr$ labeled stem cell derived exosomes were injected intravenously into the mouse, and subsequently imaged thirty minutes after the injection, shown in PET image 500. Illustrated in PET image 500, and also the other PET images 502,504,506, are "hotspots" of the administered $^{89}Zr$ labeled stem cell derived exosomes (homing agent mediated accumulation zones of the $^{89}Zr$ labeled exosomes) at specific locations within the mouse (e.g., the heart 510, the liver 512, and the gut 514). Then, 19 hours after administering the $^{89}Zr$ labeled stem cell derived exosomes, 1% methylene blue (in Lactated Ringer's Solution) was injected in a hind paw and a front paw of the mouse and imaged 3 h post-methylene blue injection showing homing of exosome to hind paw (at reference numeral 516) and front paw (at reference numeral 518) (in PET image 502). Thus, the $^{89}Zr$ labeled stem cell derived exosomes were effectively homed to the tissue that contained methylene blue. After administering the methylene blue solution, 20 additional hours were lapsed before completing a second imaging of the mouse (at PET image 504). As illustrated in PET image 504, the methylene blue injection sites (e.g., 516, 518) show persistence of signal from 89Zr labeled stem cell derived exosomes in hind paw and front paw. Then, immediately after acquiring PET image

504, the mouse was injected with the methylene blue solution at the hind paw (designated numeral 520), opposite the first hind paw injected with methylene blue (designated numeral 516). One hour after the second injection at the opposite hind paw at reference numeral 520, PET image 506 was acquired. As illustrated in PET images 504, 506 the $^{89}$Zr labeled stem cell derived exosomes accumulated at the target site 520 even days (e.g., two days) after the injection of the $^{89}$Zr linked stem cell derived exosomes. Thus, PET images 500,502,504,506 show that the signal at the targeted site persisted, and that there remains a residual mobilizable pool of labeled exosomes (e.g., $^{89}$Zr linked stem cell derived exosomes) to at least 2 days after administration.

Figure 13:
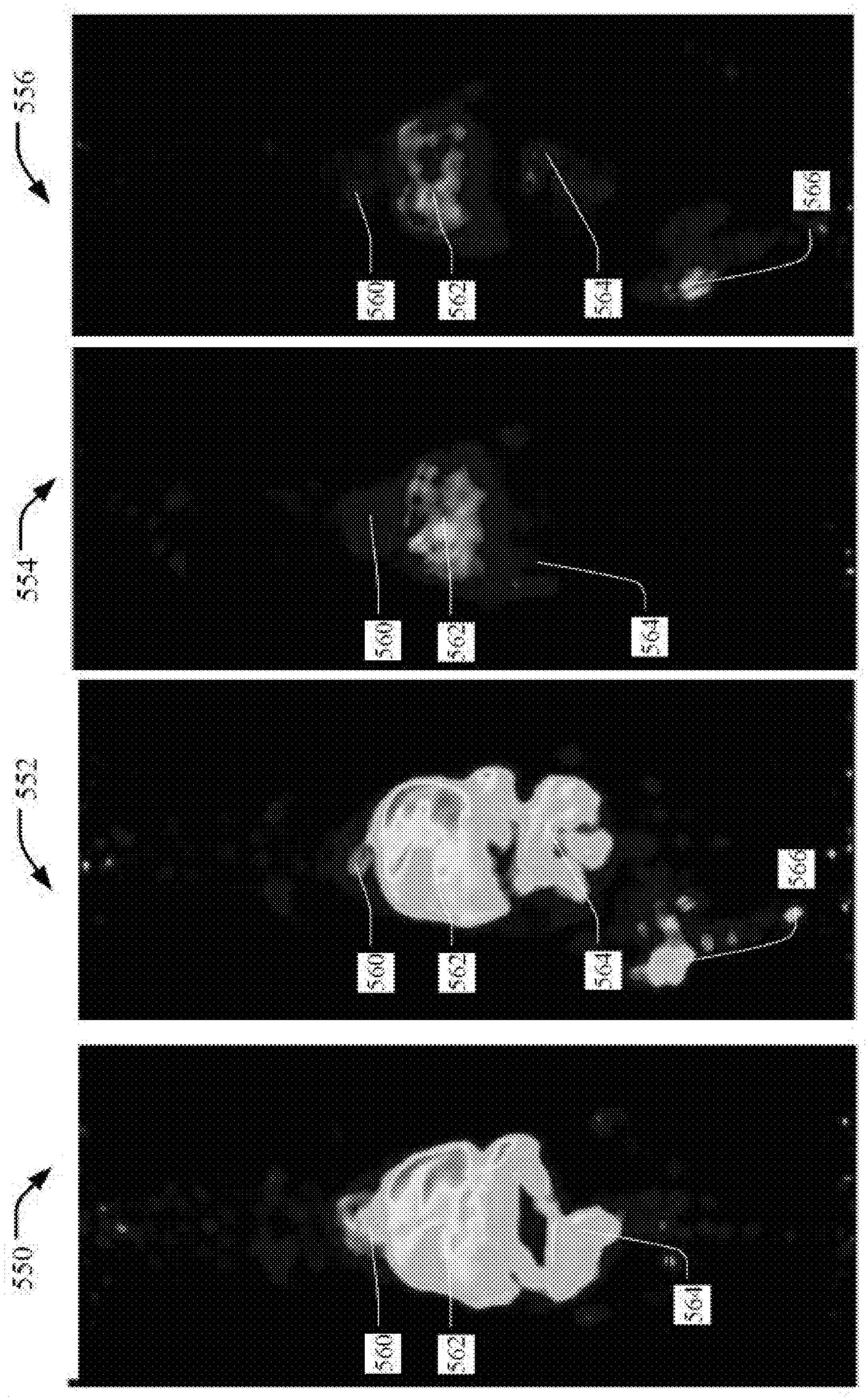
FIG. 13 shows positron emission tomography ("PET") images of an experiment using injected radiolabeled exosomes derived from A549 lung cancer cells, and SK-N-SH brain-bone marrow cancer cells, and also using a derivative of phenothiazine, methylene blue.

FIG. 13 illustrates methylene blue was able to home exosomes irrespective of their cellular origin. PET image 550 and 554 was taken one hour after the mouse was intravenously injected (via tail vein) with the $^{89}$Zr labeled A549 lung cancer derived exosomes and SK-N-SH brain cancer (bone marrow metastasis) derived exosomes, respectively. These functioned as a control (e.g., did not receive methylene blue). Then after one hour, 1% methylene blue (in Lactated Ringer's Solution) was injected in a hind limb paw. The opposite hind limb paw received a methylene blue-free and sterile Lactated Ringer's Solution. One hour after administering the methylene blue solution, the PET image 552 and 556 was taken. As illustrated in the PET image 552 (for A549 cells derived exosomes) and 556 (SK-N-SH cell derived exosomes), the hind paw that received the methylene blue injection, indicated by the reference numeral 566, shows a significant accumulation of the $^{89}$Zr labeled cancer cell derived exosomes. Conversely, the opposite paw, which received the methylene blue-free Lactated Ringer's Solution, did not show an accumulation of the $^{89}$Zr linked cancer cell derived exosomes. Thus, the methylene blue homed the $^{89}$Zr labeled A549 and SK-N-SH derived exosomes from circulation showing that it can home extracellular vesicles independent of their cellular origin.

Thus, the invention provides extracellular vesicle-homing compounds.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The invention claimed is:

1. A method for treating a medical condition in a subject, the method comprising:

(a) administering to the subject a homing agent at an administration site, wherein the homing agent is poly (ethylene glycol); and (b) administering to the subject a structure comprising a bioactive agent thereby associating naturally occurring extracellular vesicles already present within the subject with the bioactive agent and waiting a time sufficient such that the naturally occurring extracellular vesicles within the subject are homed to the homing agent in the subject, wherein the administration site is at least one of a tissue, a blood vessel, or a lymph vessel.

2. The method of claim 1, wherein the subject has a diseased tissue, the diseased tissue being at least one of a tumor, an inflammation, an injury, and an infection, wherein the diseased tissue produces disease derived extracellular vesicles within the subject, wherein, following administration of the homing agent, the disease derived extracellular vesicles are homed to the homing agent in the subject, thereby disrupting disease-promoting actions of the disease derived extracellular vesicles in the subject either by preventing the disease derived extracellular vesicles from traveling to or traveling from the diseased site.

3. The method of claim 1, further comprising removing a tissue or a bodily fluid of the subject that contains naturally occurring extracellular vesicles.

4. The method of claim 3, further comprising injecting healthy extracellular vesicles into the subject, and wherein injecting healthy extracellular vesicles occurs after the tissue or the bodily fluid has been removed.

5. The method of claim 1, wherein the molecular weight of the homing agent is 150 to 2000 Daltons.

6. The method of claim 1, wherein the homing agent has the Formula (I):

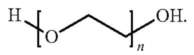

(I)

n = 3-45

7. The method of claim 1, further comprising administering a radioisotope selected from the group consisting of $^{11}$C, $^{13}$N, $^{15}$O, $^{18}$F, $^{34m}$Cl, $^{38}$K, $^{45}$Ti, $^{51}$Mn, $^{52m}$Mn, $^{52}$Fe, $^{55}$Co, $^{60}$Cu, $^{61}$Cu, $^{62}$Cu, $^{64}$Cu, $^{66}$Ga, $^{68}$Ga, $^{71}$As, $^{72}$As, $^{74}$As, $^{211}$At, $^{75}$Br, $^{76}$Br, $^{82}$Rb, $^{43}$Sc, $^{44}$Sc, $^{86}$Y, $^{89}$Zr, $^{90}$Nb, $^{94m}$Tc, $^{110m}$In, $^{118}$Sb, and $^{124}$I.

8. The method of claim 1 wherein:

the bioactive agent includes a therapeutic agent.

9. The method of claim 8 wherein:

the medical condition is diabetes.

10. A method for treating a medical condition in a subject, the method comprising:

(a) administering to the subject an amount of homing agent at an administration site, wherein the homing agent is poly(ethylene glycol);

(b) administering to the subject extracellular vesicles, each of the extracellular vesicles being associated with a bioactive agent; and (c) waiting a time sufficient such that the administered extracellular vesicles are homed to the homing agent in the subject.

11. The method of claim 10, wherein the bioactive agent includes a cytotoxic agent and/or a therapeutic agent.

12. The method of claim 10, wherein a molecular weight of the homing agent is 150 to 2000 Daltons.

13. The method of claim 10, wherein the homing agent has the Formula (I):

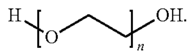

(I)

n = 3-45

14. The method of claim 10 wherein:

the medical condition is diabetes.

15. A method for treating a medical condition in a subject, the method comprising:

(a) administering to the subject an amount of a homing agent, wherein the homing agent is a derivative of poly(ethylene glycol), and wherein at least one atom in the derivative of poly(ethylene glycol) is associated with a biological targeting agent defining a targeted homing agent, the biological targeting agent allowing targeting of the homing agent to a specific location within the subject;

(b) waiting a time sufficient to allow the targeted homing agent to accumulate at the specific location within the subject, due to the biological targeting agent associated with the homing agent; and (c) administering to the subject a structure comprising a bioactive agent and optionally administering extracellular vesicles to the subject;

thereby associating naturally occurring extracellular vesicles already present within the subject with the bioactive agent and waiting a time sufficient such that the naturally occurring extracellular vesicles (EVs) within the subject, and/or administered EVs accumulate at the specific location of the subject, due to the homing of the extracellular vesicles to the homing agent of the targeted homing agent.

16. The method of claim 15, wherein a molecular weight of the homing agent is 150 to 2000 Daltons.

17. The method of claim 15, wherein the derivative of poly(ethylene glycol) is a derivative of the Formula (I):

(I)

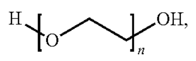

n = 3-45 and the biological targeting agent is covalently linked to the at least one atom in the derivative of poly(ethylene glycol).

18. The method of claim 12, further comprising administering a radioisotope selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{211}At$, $^{75}Br$, $^{76}Br$, $^{82}Rb$, $^{43}Sc$, $^{44}Sc$, $^{86}Y$, $^{89}Zr$, $^{90}Nb$, $^{94m}Tc$, $^{110m}In$, $^{118}Sb$, and $^{124}I$.

19. The method of claim 15 wherein:

the bioactive agent includes a therapeutic agent.

20. The method of claim 19 wherein:

the medical condition is diabetes.

21. A method for treating a medical condition in a subject, the method comprising:

(a) administering to the subject a homing agent, wherein the homing agent is a derivative of poly(ethylene glycol), and wherein at least one atom in the derivative of poly(ethylene glycol) is associated with a biological targeting agent defining a targeted homing agent, the biological targeting agent allowing targeting of the homing agent to a specific location within the subject;

(b) waiting a time sufficient to allow the targeted homing agent to accumulate at the specific location within the subject, due to the biological targeting agent associated with the homing; and (c) administering to the subject a structure comprising a bioactive agent thereby associating naturally occurring extracellular vesicles already present within the subject with the bioactive agent and waiting a time sufficient such that the naturally occurring extracellular vesicles within the subject accumulate at the specific location of the subject, due to the homing of the extracellular vesicles to the targeted homing agent.

22. The method of claim 21, wherein the derivative of poly(ethylene glycol) is a derivative of the Formula (I):

(I)

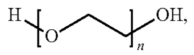

n = 3-45 and the biological targeting agent is covalently linked to the at least one atom in the derivative of poly(ethylene glycol).

23. The method of claim 21, further comprising administering a radioisotope selected from the group consisting of $^{11}C$, $^{13}N$, $^{15}O$, $^{18}F$, $^{34m}Cl$, $^{38}K$, $^{45}Ti$, $^{51}Mn$, $^{52m}Mn$, $^{52}Fe$, $^{55}Co$, $^{60}Cu$, $^{61}Cu$, $^{62}Cu$, $^{64}Cu$, $^{66}Ga$, $^{68}Ga$, $^{71}As$, $^{72}As$, $^{74}As$, $^{211}At$, $^{75}Br$, $^{76}Br$, $^{82}Rb$, $^{43}Sc$, $^{44}Sc$, $^{86}Y$, $^{89}Zr$, $^{90}Nb$, $^{94m}Tc$, $^{110m}In$, $^{118}Sb$, and $^{124}I$.

24. The method of claim 21 wherein:

the bioactive agent includes a therapeutic agent.

25. The method of claim 24 wherein:

the medical condition is diabetes.

26. A method for treating a medical condition in a subject, the method comprising:

(a) administering to the subject a homing agent, wherein the homing agent is a derivative of poly(ethylene glycol), and wherein at least one atom in the derivative of poly(ethylene glycol) is associated with an associated biological targeting agent defining a targeted homing agent, the biological targeting agent allowing targeting of the homing agent to a specific location within the subject;

(b) associating extracellular vesicles with a bioactive agent and administering to the subject the extracellular vesicles;

(c) waiting a time sufficient to allow the targeted homing agent to accumulate at the specific location within the subject, due to the biological targeting agent associated with the homing agent;

(d) waiting a time sufficient such that the administered extracellular vesicles home to the specific location within the subject, due to the homing of the extracellular vesicles to the homing agent of the targeted homing agent.

27. The method of claim 26, wherein the derivative of poly(ethylene glycol) is a derivative of the Formula (I):

(I)

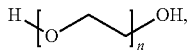

n = 3-45 and the biological targeting agent is covalently linked to the at least one atom in the derivative of poly(ethylene glycol).

28. The method of claim 26 wherein:

the bioactive agent includes a therapeutic agent.

29. The method of claim 28 wherein:

the medical condition is diabetes.

* * * * *